US009708249B1

(12) United States Patent
Goyal et al.

(10) Patent No.: US 9,708,249 B1
(45) Date of Patent: Jul. 18, 2017

(54) COMPOSITIONS AND METHODS RELATED TO THE PRODUCTION OF ACRYLONITRILE

(71) Applicant: Southern Research Institute, Birmingham, AL (US)

(72) Inventors: Amit Goyal, Cary, NC (US); Jadid Samad, Durham, NC (US)

(73) Assignee: Southern Research Institute, Birmingham, AL (US)

(*) Notice: Subject to any disclaimer, the term of this patent is extended or adjusted under 35 U.S.C. 154(b) by 0 days.

(21) Appl. No.: 15/245,835

(22) Filed: Aug. 24, 2016

(51) Int. Cl.
| B01J 23/888 | (2006.01) |
| B01J 23/30 | (2006.01) |
| B01J 21/04 | (2006.01) |
| C07C 253/26 | (2006.01) |
| C07C 45/66 | (2006.01) |
| C07C 45/00 | (2006.01) |
| C07C 29/10 | (2006.01) |
| B01J 23/89 | (2006.01) |

(52) U.S. Cl.
CPC .......... *C07C 253/26* (2013.01); *B01J 21/04* (2013.01); *B01J 23/30* (2013.01); *B01J 23/888* (2013.01); *B01J 23/892* (2013.01); *B01J 23/8926* (2013.01); *C07C 29/103* (2013.01); *C07C 45/002* (2013.01); *C07C 45/66* (2013.01)

(58) Field of Classification Search
None
See application file for complete search history.

(56) References Cited

U.S. PATENT DOCUMENTS

| 5,977,013 | A | 11/1999 | Elliott et al. |
| 7,790,934 | B2 | 9/2010 | Redlingshofer et al. |
| 7,846,861 | B2 | 12/2010 | Redlingshofer et al. |
| 8,378,136 | B2 | 2/2013 | Dubois |
| 8,461,380 | B2 | 6/2013 | Aoki et al. |
| 8,530,697 | B2 | 9/2013 | Dubois et al. |
| 2003/0119952 | A1 | 6/2003 | Werpy et al. |
| 2014/0206831 | A1 | 7/2014 | Venkitasubramanian |

FOREIGN PATENT DOCUMENTS

GB          897226 A       5/1962

OTHER PUBLICATIONS

Abraham, D. S., "Production of propylene oxide from propylene glycol" Master's Thesis University of Missouri-Columbia (2007) (75 pages).
Acrylonitrile by propene ammoxidation, http://tekim.undip.ac.id/staf/istadi/files/2009/05/topik51.pdf (2009) (26 pages).
Adams et al, "Investigation of the Mechanism of Catalytic Oxidation of Proylene to Acrolein and Acryonitrile,"Journal of Catalysis. (1963) 2, 63-68.
Benchaita, T., "Greenhouse gas emissions from new petrochemical plants", Technical Note No. IDB-TN-562 (2013) (84 pages).
Copeland, J. R., et al, "Surface Interactions of $C_2$ and $C_3$ Polyols with $\gamma$-$Al_2O_3$ and the Role of Coadsorbed Water", Langmuir (2013) 29, 581-593.
Cutrufello, M. G., et al, "Acid-Base Properties of Zirconium, Cerium and Lanthanum Oxides by Calorimetric and Catalytic Investigation", Topics in Catalysis (2002) 19, 3-4, 225-240.
Dar, A.B., et al, "Vapour Phase Conversion of Glycerol to Acrolein over Supported Copper", Arab J Sci Eng. (2013) 38, 37-40.
Dasari, M.A., et al, "Low-Pressure Hydrogenolysis of Glycerol to Propylene Glycol", Applied Catalysis A: General (2005) 281 225-23.
Eriksson, Ö. Goring, "Structural studies on the chemical bonds between lignins and carbohydrates in spruce wood", Wood Science and Technology (1980) 14, 267-279.
Gallezot, P., et al, "Glucose hydrogenation on promoted raney-nickel catalysts", Journal of Catalysis. (1994) 146, 93-102.
Garrote, G., et al, "Mild autohydrolysis: an environmentally friendly technology for xylooligosaccharide production from wood", Journal of Chemical and Biotechnology (1999) 74, 1101-1109.
Goyal, A., et al, Functional Fillers for Plastics, Chapter 10, Carbon Nanotubes/Nanofibers and Carbon Fibers, (2010) (35 pages).
Husman, "Development and Commercialization of a Novel Low-Cost Carbon Fiber", Zoltek Companies, Inc., May 16, 2012 (21 pages).
JCATI Funded Research (2016) available at: http://www.jcati.org/funding/jcati-funded-research (8 pages).
Jubb, Charles et al, "IPCC guidelines for national greenhouse gas inventories: Industrial processes and product use, Chapter 3: Chemical industry emissions" (2006), (110 pages).
Li, Z., et al, "Dehydration and dehydrogenation of ethylene glycol on rutile $TiO_2$ (110)", Phys. Chem. Chem. Phys. (2013) 15, 12180-12186.
Liebig, C., et al, "Glycerol conversion to acrylonitrile by consecutive dehydration over $WO_3$/$TiO_2$ and ammoxidation over Sb-(Fe,V)-O", Applied Catalysis B: Environmental (2013) 132-133, pp. 170-182.
Niemelä, K., et al, (1999) "Characterization of pulping liquors", Analytical Methods in Wood Chemistry, Pulping and Papermaking. pp. 193-231, Springer-Verlag, Berlin.
Oka, H., et al, "Ammoxidation of Acrolein on Catalyst of Fe—Bi—P. Mixed Oxide System," Journal of Applied Chemistry and Biotechnology (1975) 25, 663-670.
Olga, M., et al, "New Reaction: Conversion of Glycerol into Acrylonitrile," Chem. Sus. Chem. (2008) 1, 511-513.
Palmqvist, E., et al, "Fermentation of lignocellulosic hydrolysates. II: inhibitors and mechanisms of inhibition", Bioresource Technology (2000) 74, pp. 25-33.
Ravenelle, R.M., et al, "Effects of Metal Precursors on the Stability and Observed Reactivity of Pt/$\gamma$- Al 2 O3 Catalysts in Aqueous Phase Reactions," Chem Cat Chem (2012) 4, 492-494.
Ravenelle, R.M., et al, "Structural Changes of $\gamma$-$Al_2O_3$-Supported Catalysts in Hot Liquid Water", ACS Catalysis (2011) 1, pp. 552-561.

(Continued)

*Primary Examiner* — Samantha Shterengarts
(74) *Attorney, Agent, or Firm* — Ballard Spahr LLP

(57) ABSTRACT

Disclosed herein are a catalyst and method useful in the process of converting sugars to acrylonitrile.

20 Claims, 14 Drawing Sheets

(56) References Cited

OTHER PUBLICATIONS

Sugar to Polyols Process—IPCI, (2012) available at http://polyolchem.com/technology/sugar-to-polyols-process (3 pages).

Suprun, et al., (2011) "TPD-TG-MS Investigations of the Catalytic Conversion of Glycerol over $MOx$—$Al_2O_3$—$PO_4$ Catalysts", Chemical Engineering & Technology, vol. 34, Issue 1 (pp. 134-139).

Torresi, P.A., et al, "Conversion of diols by dehydrogenation and dehydration reactions on silica-supported copper catalysts", Applied Catalysis A: General (2013) 458, pp. 119-129.

Ulgen, (2009) "Conversion of glycerol to the valuable intermediates acrolein and allyl alcohol in the presence of heterogeneous catalysts", Dissertation (144 pages).

Ulgen, A., et al, "Conversion of glycerol to acrolein in the presence of $WO_3/TiO_2$ catalysts", Applied Catalysis A: General (2011) 400, pp. 34-38.

Ulgen, A., et al, "Conversion of Glycerol to Acrolein in the Presence of $WO_3/TiO_2$ Catalysts", Catalysis Letters (2009) 131, pp. 122-128.

Wang, et al., "Catalytic performance of vanadium pyrophosphate oxides (VPO) in the oxidative dehydrogenation of glycerol," Applied Catalysis A: General 376 (2010) 25-32.

Xia, S., et al, "Hydrogenolysis of glycerol over $Cu_{0.4}/Zn_{5.6-x}$ $Mg_x$ $Al_2O_{8.6}$ catalysts: The role of basicity and hydrogen spillover", Journal of Catalysis (2012) 296, pp. 1-11.

Zhang, Z., et al, "Aqueous-phase hydrogenation of lactic acid to propylene glycol", Applied Catalysis A: General (2001) 219, pp. 89-98.

COMPOSITIONS AND METHODS RELATED TO THE PRODUCTION OF ACRYLONITRILE

FEDERALLY SPONSORED RESEARCH

This invention was made with government support under DE-EE0006781 awarded by Department of Energy and the office of Energy Efficiency and Renewable Energy (DOE-EERE). The government has certain rights in the invention.

FIELD OF THE INVENTIONS

The compositions, articles, and methods disclosed herein relates to the production of acrylonitrile and other useful chemicals.

BACKGROUND

The US Department of Energy and the industrial sector anticipate an 11-18% annual increase in the market for carbon fiber, specifically driven by motivation to reduce weight for vehicles (Global market opportunities for carbon fiber: Carbon fiber world conference, Washington D.C. 2011). Currently, carbon fibers that meet specifications (250 ksi tensile strength and 25 Msi Young's modulus) for automotive applications are made from polyacrylonitrile (PAN), obtained from acrylonitrile (ACN), which is synthesized using propylene and ammonia. World ACN production in 2010 was 5.7 million tons, and is highly dependent on volatility of propylene prices. Additionally, propylene production (a byproduct of naphtha cracking for ethylene) is reducing due to growth of the natural gas based process for production of ethylene. In light of these facts and increased demand for carbon fibers, US DOE has expressed interest in making ACN precursor that can meet specifications needed for production of carbon fibers from renewable non-food biomass with a goal of $1.00/lb cost.

There is a need for improved catalysts and methods for producing ACN and intermediates to make ACN. Such a catalytic composition and method are described herein.

SUMMARY OF THE INVENTION

Disclosed herein is a method comprising the steps of: a) separating at least a portion of ethylene glycol and propylene glycol from a first product comprising ethylene glycol, propylene glycol, and glycerol, thereby producing a second product comprising glycerol; and b) contacting the second product comprising glycerol with a first catalyst composition, thereby producing a third product comprising acrolein and hydroxyacetone, wherein the first catalyst composition comprises a first catalyst having the formula:

$$M1M2_xM3_yO_z$$

wherein M1 is a metal promoting C—O cleavage,
wherein M2 is a metal with acid sites promoting dehydration,
wherein M3 is an amphoteric catalyst support, with acid and base sites,
promoting selective dehydration in conjunction with M1,
wherein x is a molar ratio from about 0.25 to about 4,
wherein y is a molar ratio from about 0.25 to about 4,
wherein z is the total amount of oxygen bound to M1, M2, and M3, and
corresponds to the sum of the oxidation states of M1, M2, and M3.

Also disclosed herein is a method comprising the step of: a) contacting propylene glycol with a third catalyst composition, thereby producing propanal, wherein the third catalyst composition consisting essentially of a third catalyst having the formula:

$$M4M5_aO_z$$

wherein M4 is a metal with acid sites promoting dehydration,
wherein M5 is an amphoteric catalyst support, with acid and base sites, promoting selective dehydration
wherein a is a molar ratio from about 0.25 to about 4,
wherein z is the total amount of oxygen bound to M4 and M5, and corresponds to the sum of the oxidation states of M4 and M5.

Additional advantages will be set forth in part in the description which follows, and in part will be obvious from the description, or can be learned by practice of the aspects described below. The advantages described below will be realized and attained by means of the chemical compositions, methods, and combinations thereof particularly pointed out in the appended claims. It is to be understood that both the foregoing general description and the following detailed description are exemplary and explanatory only and are not restrictive.

DESCRIPTION OF THE FIGURES

The accompanying figures, which are incorporated in and constitute a part of this specification, illustrate several aspects and together with the description serve to explain the principles of the invention.

Figure 1:
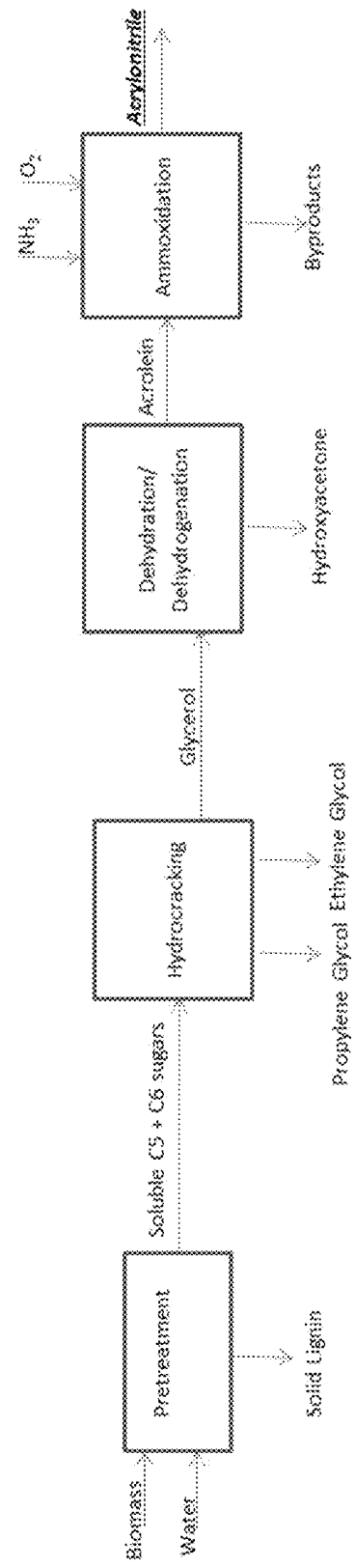
FIG. 1 shows the overall flow schematic of non-limiting aspects of the method disclosed herein for the process of producing acrylonitrile.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The disclosed methods and articles can be understood more readily by reference to the following detailed description.

Before the present compounds, compositions, articles, systems, devices, and/or methods are disclosed and described, it is to be understood that they are not limited to specific articles or methods unless otherwise specified. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

1. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

In this specification and in the claims which follow, reference will be made to a number of terms which shall be defined to have the following meanings:

It must be noted that, as used in the specification and the appended claims, the singular forms "a," "an" and "the" include plural referents unless the context clearly dictates otherwise. Thus, for example, reference to "a therapeutic agent" includes mixtures of therapeutic agents, reference to "a pharmaceutical carrier" includes mixtures of two or more such carriers, and the like].

"Optional" or "optionally" means that the subsequently described event or circumstance can or cannot occur, and that the description includes instances where the event or circumstance occurs and instances where it does not. For example, the phrase "optionally comprising an adhesive material" means that the adhesive material can or cannot be present and that the description includes both situations.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

A weight percent (wt. %) of a component, unless specifically stated to the contrary, is based on the total weight of the therapeutic composition or composition or material, in which the component is included.

References in the specification and concluding claims to parts by weight, of a particular element or component in a composition or article, denote the weight relationship between the element or component and any other elements or components in the composition or article for which a part by weight is expressed. Thus, in a composition containing 2 parts by weight of component X and 5 parts by weight component Y, X and Y are present at a weight ratio of 2:5, and are present in such ratio regardless of whether additional components are contained in the composition.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

2. Production of Intermediates to Produce Acrylonitrile

Micron-sized carbon fibers presently used are mostly produced by heat treatment or controlled pyrolysis of different precursor fibers. The most prevalent precursors are PAN, cellulose fibers (such as viscose, rayon, and cotton), petroleum and coal tar pitch, and certain phenolic fibers. Synthesis process involves heat treatment, oxidative stabilization, carbonization and graphitization to achieve desired mechanical strength. It is well established in the literature that strength of fibers is the function of crystallinity and orientation, and by reducing defects in the fiber. The best way to achieve this is to start with a highly oriented precursor and then maintain the initial high orientation during the process of stabilization and carbonization through tension (http://tekim.undip.ac.id/staf/istadi/files/2009/05/topik51.pdf).

PAN has highly polar nitrile groups which cause strong dipole-dipole forces that act as cross-links, making the polymer soluble only in highly ionizing solvents, increasing its melting point, and making it more suitable as a carbon fiber precursor. In order to obtain PAN which results in such fiber properties, precursor ACN is required which is obtained from ammoxidation of propylene (petrochemical). The production of ACN accounts for approximately 70% of total cost, which is highly volatile with price currently ranging between $1,000 to 1,400/MT.

Recent advances have been made to produce ACN from glycerol (Olga, M., et al, Chem. Sus. Chem. (2008) 1, 511-513; Liebig, C., et al, Applied Catalysis B: Environmental (2013) 132-133, 170-182; Ulgen et. al. Catalysis Letters. 2009, 131: 122-128; Ulgen et. al. Applied catalysis A. General 400 (2011), 34-38), which can be sourced as a byproduct from biodiesel plants. While glycerol is available from subsidized biodiesel plants, for a long term solution, suitable renewable feed stocks and conversion process are needed.

It is known that propylene ammoxidation proceeds through an allylic intermediate acrolein. This ammoxidation was studied as early as 1963 by Adams et al over traditional Bismuth molybdate catalysts (Adams et al, Journal of Catalysis. (1963) 2, 63-68; http://www1.eere.energy.gov/vehiclesandfuels/pdfs/merit_review_2012/lightweight_materials/1 m048_husman_2012_o.pdf). A renewed interest in acrolein ammoxidation has emerged due to high availability of glycerol as a byproduct from bio-diesel plants. Glycerol can be readily dehydrated to form acrolein; however biodiesel plants are fast disappearing due to lack of subsidies. Thus, a constant source and pure glycerol is not available nor is the process economically attractive, ACN produced from glycerol costs~$2200/MT.

Disclosed herein is a catalyst and method that derive acrolein from glycerol. The catalyst and method can be used with inexpensive starting materials, such as sugars, e.g. hemicellulose or cellulose sugars (cost around 5 to 40 cents/kg). The produced acrolein can in turn be converted to ACN. A schematic flow of the process to convert biomass to ACN is shown in FIG. 1.

Also disclosed herein is a catalyst that derives propanal from propylene glycol. Propanal can in turn be converted several other C3 chemicals, such as, for example, propionic acid.

A method of using sugars from sugars such as hemicellulose or cellulose derived sugars to produce polyols, e.g. ethylene glycol, propylene glycol, and glycerol, to form acrolein and hydroxyacetone (also known as acetol) is disclosed herein. The method disclosed herein includes the step of separating out ethylene glycol and propylene glycol to leave behind a product comprising glycerol. Such a method is desired because of its low carbon footprint and economic viability.

Also disclosed herein is a multifunctional catalyst capable of, in a single step, converting C5 and C6 sugars to ethylene glycol, propylene glycol, and glycerol. In one aspect, the, C5 and C6 sugars are hemicellulose or cellulose derived C5 and C6 sugars from biomass.

a. First Catalyst Composition

The first catalyst disclosed herein can convert glycerol to a product comprising acrolein and hydroxyacetone. Such product mixture is desired because hydroxyacetone can easily be separated from the acrolein by use of low energy distillation or flash vaporization. ACN can then be produced by ammoxidizing acrolein in presence of ammonia and oxygen (air).

Disclosed herein is a first catalyst composition for converting glycerol to acrolein and hydroxyacetone comprising a first catalyst having the formula:

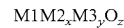

wherein M1 is a metal promoting C—O cleavage, wherein M2 is a metal with acid sites promoting dehydration, wherein M3 is an amphoteric catalyst support, with acid and base sites, promoting dehydration in conjunction with M1, wherein x is a molar ratio from about 0.25 to about 4, wherein y is a molar ratio from about 0.25 to about 4, wherein z is the total amount of oxygen bound to M1, M2, and M3, and corresponds to the sum of the oxidation states of M1, M2, and M3.

In the formula M1M2$_x$M3$_y$O$_z$, the metals M1, M2, and M3 are different metals.

The catalyst composition comprises metals that advantageously C—O cleavage (M1) and then dehydrate (M2, M3) triols, such as, for example, glycerol. As such the catalyst composition can convert glycerol to acrolein to hydroxyacetone. These conversions are desired as hydroxyacetone can easily be separated from acrolein due to their different boiling temperatures.

M1 is a metal promoting C—O cleavage in molecules, such as, for example, C—O cleavage in triols, such as, for example, glycerol. In one aspect, M1 is selected from the group consisting of Cu, Zn, and Sn. For example, M1 can be Cu. In another example, M1 can be Zn. In yet another example, M1 can be Sn.

M2 is a metal with acid sites promoting dehydration in molecules, such as, for example, dehydration in triols, such as, for example, glycerol. In one aspect, M2 is selected from the group consisting of W, Fe, P, and a zeolite. For example, M2 can be W. In another example, M2 can be Fe. In yet another example, M2 can be P. In yet another example, M2 can be a zeolite.

M3 is an amphoteric catalyst support, with acid and base sites, promoting selective dehydration in conjunction with M1 in molecules, such as, for example, dehydration in conjunction with M1 in triols, such as, for example, glycerol. In one aspect, M3 is selected from the group consisting of Zr, Al, Si, Mg, Ti, La, and Ce. For example, M3 can be Zr. In another example, M3 can be Al. In yet another example, M3 can be Si. In yet another example, M3 can be Mg. In yet another example, M3 can be a Ti. In yet another example, M3 can be a La. In yet another example, M3 can be a Ce. Selection of M3 can be dictated by the support's stability in steam phase conditions. For example, alumina can be modified using silica as described by Ravenelle et al (Ravenelle, R. M., et al, ACS Catalysis (2011) 1, 552-561; Ravenelle, R. M., et al, Chem Cat Chem (2012) 4, 492-494).

In one aspect, M1 can be Cu, M2, can be W, and M3 is selected from the group consisting of Zr, Al, Si, Mg, Ti, La, and Ce. In another aspect, M1 can be Cu, M2, can be selected from the group consisting of W, Fe, P, and a zeolite, and M3 can be Zr. In yet another aspect, M1 can be selected from the group consisting of Cu, Zn, and Sn, M2, can be W, and M3 can be Zr.

In one aspect, M1 can be Cu, M2 can be selected from the group consisting of W, Fe, P, and a zeolite, and M3 can be selected from the group consisting of Zr, Al, Si, Mg, Ti, La, and Ce. In another aspect, M1 can be selected from the group consisting of Cu, Zn, and Sn, M2 can be W, and M3 can be selected from the group consisting of Zr, Al, Si, Mg, Ti, La, and Ce. In yet another aspect, M1 can be selected from the group consisting of Cu, Zn, and Sn, M2 can be selected from the group consisting of W, Fe, P, and a zeolite, and M3 can be Zr.

In one aspect, x is a molar ratio from about 0.25 to about 4. In another aspect, x is a molar ratio from about 0.8 to about 4. In yet another aspect, x is a molar ratio from about 1.8 to about 4. In yet another aspect, x is a molar ratio from about 0.25 to about 3. In yet another aspect, x is a molar ratio from about 0.25 to about 2.2. In yet another aspect, x is a molar ratio from about 0.8 to about 2.2.

In one aspect, y is a molar ratio from about 0.25 to about 4. In another aspect, y is a molar ratio from about 0.8 to about 4. In yet another aspect, y is a molar ratio from about 1.8 to about 4. In yet another aspect, y is a molar ratio from about 0.25 to about 3. In yet another aspect, y is a molar ratio from about 0.25 to about 2.2. In yet another aspect, y is a molar ratio from about 0.8 to about 2.2.

In one aspect, z is the total amount of oxygen bound to M1, M2, and M3, and corresponds to the sum of the oxidation states of M1, M2, and M3. It is known in the art how to determine z based on the oxidation state of M1, M2, and M3.

In one aspect, M1 and M2, together with their respective amounts of oxygen based on oxidation state, are present in an amount from 1 wt % to 40 wt % of the catalyst wherein the support M3 provides the balance wt %. In another aspect, M1 and M2, together with their respective amounts of oxygen based on oxidation state, are present in an amount from 1 wt % to 30 wt % of the catalyst wherein the support M3 provides the balance wt %. M1 and M2, together with their respective amounts of oxygen based on oxidation state, are present in an amount from 1 wt % to 20 wt % of the catalyst wherein the support M3 provides the balance wt %. M1 and M2, together with their respective amounts of oxygen based on oxidation state, are present in an amount from 5 wt % to 20 wt % of the catalyst wherein the support M3 provides the balance wt %.

In one aspect, the catalyst has the formula $CuOWO_3ZrO_2$. In another aspect, the catalyst has the formula $CuOWO_3TiO_2$. In another aspect, the catalyst has the formula $CuOWO_3SiO_2$.

The catalyst can be produced using co-impregnation of metal salts on acid supports, followed by calcination, which is typically performed at a temperature between 300° C. to 600° C., such as about 450° C.

b. Second and Third Catalyst

The second and third catalyst disclosed herein can convert propylene glycol to a product comprising propanal or consisting essentially of propanal. Such product increases the by-product yield and thus helps in carbon conservation. Furthermore it monetizes the principle product being acrylonitrile. In addition, propanal is an intermediate that can be used to produce several C3 chemicals, such as, for example, propionic acid.

Disclosed herein is a second catalyst composition for converting propylene glycol to propanal comprising a second catalyst having the formula:

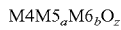

$$M4M5_aM6_bO_z$$

wherein M4 is a metal with acid sites promoting dehydration,
wherein M5 is an amphoteric catalyst support, with acid and base sites, promoting selective dehydration in conjunction with M6 when present,
wherein M6 is a metal promoting C—O cleavage,
wherein a is a molar ratio from about 0.25 to about 4,
wherein b is a molar ratio from 0 to about 4,
wherein z is the total amount of oxygen bound to M4, M5, and M6, and corresponds to the sum of the oxidation states of M4, M5, and M6.

Also disclosed herein is a third catalyst composition for converting propylene glycol to propanal consisting essentially of a third catalyst having the formula:

$$M4M5_aO_z$$

wherein M4 is a metal with acid sites promoting dehydration,
wherein M5 is an amphoteric catalyst support, with acid and base sites, promoting selective dehydration,
wherein a is a molar ratio from about 0.25 to about 4,
wherein z is the total amount of oxygen bound to M4 and M5, and corresponds to the sum of the oxidation states of M4 and M5.

In the formula of the second catalyst $M4M5_aM6_bO_z$, the metals M4, M5, and M6 are different metals.

In the formula of the third catalyst $M4M5_aO_z$, the metals M4 and M5 are different metals.

The catalyst composition comprises metals that advantageously dehydrate (M4, M5) and promote C—O cleavage (M6) in diols, such as, for example, propylene glycol. As such the catalyst composition can convert propylene glycol to propanal. These conversions are desired as propanal can in turn be converted to acrolein.

M4 is a metal with acid sites promoting dehydration in molecules, such as, for example, dehydration in diols, such as, for example, propylene glycol. In one aspect, M4 is selected from the group consisting of W, Fe, P, and a zeolite. For example, M4 can be W. In another example, M4 can be Fe. In yet another example, M4 can be P. In yet another example, M4 can be a zeolite.

M5 is an amphoteric catalyst support, with acid and base sites, promoting dehydration in conjunction with M6 when present in molecules, such as, for example, C—O cleavage in conjunction with M6 when present in diols, such as, for example, propylene glycol. In one aspect, M5 is selected from the group consisting of Zr, Al, Si, Mg, Ti, La, and Ce. For example, M5 can be Zr. In another example, M5 can be Al. In yet another example, M5 can be Si. In yet another example, M5 can be Mg. In yet another example, M5 can be a Ti. In yet another example, M5 can be a La. In yet another example, M5 can be a Ce. Selection of M5 can be dictated by the support's stability in steam phase conditions. For example, alumina can be modified using silica as described by Ravenelle et al (Ravenelle, R. M., et al, ACS Catalysis (2011) 1, 552-561; Ravenelle, R. M., et al, Chem Cat Chem (2012) 4, 492-494).

M6 is a metal promoting C—O cleavage in molecules, such as, for example, C—O cleavage in diols, such as, for example, propylene glycol. In one aspect, M6 is selected from the group consisting of Cu, Zn, and Sn. For example, M6 can be Cu. In another example, M6 can be Zn. In yet another example, M6 can be Sn.

For the second catalyst of formula $M4M5_aM6_bO_z$: In one aspect, M4 can be W, M5 is selected from the group consisting of Zr, Al, Si, Mg, Ti, La, and Ce, and M6 can be present and be Cu. In another aspect, M4 can be selected from the group consisting of W, Fe, P, and a zeolite, M5 can be Zr, and M6 can be present and be Cu. In yet another aspect, M4 can be W, M5 can be Zr, and M6 can be present and be selected from the group consisting of Cu, Zn, and Sn.

For the second catalyst of formula $M4M5_aM6_bO_z$: In one aspect, M4 can be selected from the group consisting of W, Fe, P, and a zeolite, M5 can be selected from the group consisting of Zr, Al, Si, Mg, Ti, La, and Ce, and M6 can be present and be Cu. In another aspect, M4 can be W, M5 can be selected from the group consisting of Zr, Al, Si, Mg, Ti, La, and Ce, and M6 can be selected from the group consisting of Cu, Zn, and Sn. In yet another aspect, M4 can be selected from the group consisting of W, Fe, P, and a zeolite, M5 can be Zr, and M6 can be selected from the group consisting of Cu, Zn, and Sn.

For the third catalyst of formula $M4M5_aO_z$: In one aspect, M4 can be W, and M5 is selected from the group consisting of Zr, Al, Si, Mg, Ti, La, and Ce. In another aspect, M4 can be selected from the group consisting of W, Fe, P, and a zeolite and M5 can be Zr. In yet another aspect, M4 can be W and M5 can be Zr.

In one aspect, a is a molar ratio from about 0.25 to about 4. In another aspect, a is a molar ratio from about 0.8 to about 4. In yet another aspect, a is a molar ratio from about 1.8 to about 4. In yet another aspect, a is a molar ratio from about 0.25 to about 3. In yet another aspect, a is a molar ratio from about 0.25 to about 2.2. In yet another aspect, a is a molar ratio from about 0.8 to about 2.2.

In one aspect, b is a molar ratio from about 0.25 to about 4. In another aspect, b is a molar ratio from about 0.8 to about 4. In yet another aspect, b is a molar ratio from about 1.8 to about 4. In yet another aspect, b is a molar ratio from about 0.25 to about 3. In yet another aspect, b is a molar ratio from about 0.25 to about 2.2. In yet another aspect, b is a molar ratio from about 0.8 to about 2.2.

In one aspect, z is the total amount of oxygen bound to M4, M5, and M6, and corresponds to the sum of the oxidation states of M4, M5, and M6. It is known in the art how to determine z based on the oxidation state of M4, M5, and M6.

In one aspect, z is the total amount of oxygen bound to M4 and M5, and corresponds to the sum of the oxidation states of M4 and M5. It is known in the art how to determine z based on the oxidation state of M4 and M5.

In one aspect, the second catalyst has the formula $CuOWO_3ZrO_2$. In another aspect, the second catalyst has the formula $CuOWO_3TiO_2$. In another aspect, the second catalyst has the formula $CuOWO_3SiO_2$.

In one aspect, the third catalyst has the formula $WO_3ZrO_2$. In another aspect, the third catalyst has the formula $WO_3TiO_2$. In another aspect, the third catalyst has the formula $WO_3SiO_2$.

The catalyst can be produced using co-impregnation of metal salts on acid supports, followed by calcination, which is typically performed at a temperature between 300° C. to 600° C., such as about 450° C.

c. Method

The method disclosed herein reduces the steps needed to convert biomass to useful products such as ethylene glycol, propylene glycol, glycerol, propanal, acrolein, and acrylonitrile. As a result, the method further reduces the greenhouse gas emission as compared to previously known processes.

I. Production of Ethylene Glycol, Propylene Glycol, and Glycerol

Disclosed herein is a method that converts sugars, such as C5 and/or C6 sugars to ethylene glycol, propylene glycol, and glycerol.

Disclosed herein is a method comprising the step of: a) in a single step, converting C5 and/or C6 sugars to a first product comprising ethylene glycol, propylene glycol, and glycerol in the presence of a multifunctional catalyst.

In one aspect, the C5 and/or C6 sugars can be C5 and/or C6 hemicellulose and cellulose derived sugars. The C5 and/or C6 sugars or C5 and/or C6 hemicellulose and cellulose derived sugars can be produced from any type of biomass. Biomass is known in the art and is biological material derived from living, or recently living organisms. The process of producing C5 and/or C6 sugars or C5 and/or C6 hemicellulose and cellulose derived sugars from biomass is known in the art.

Figure 3:
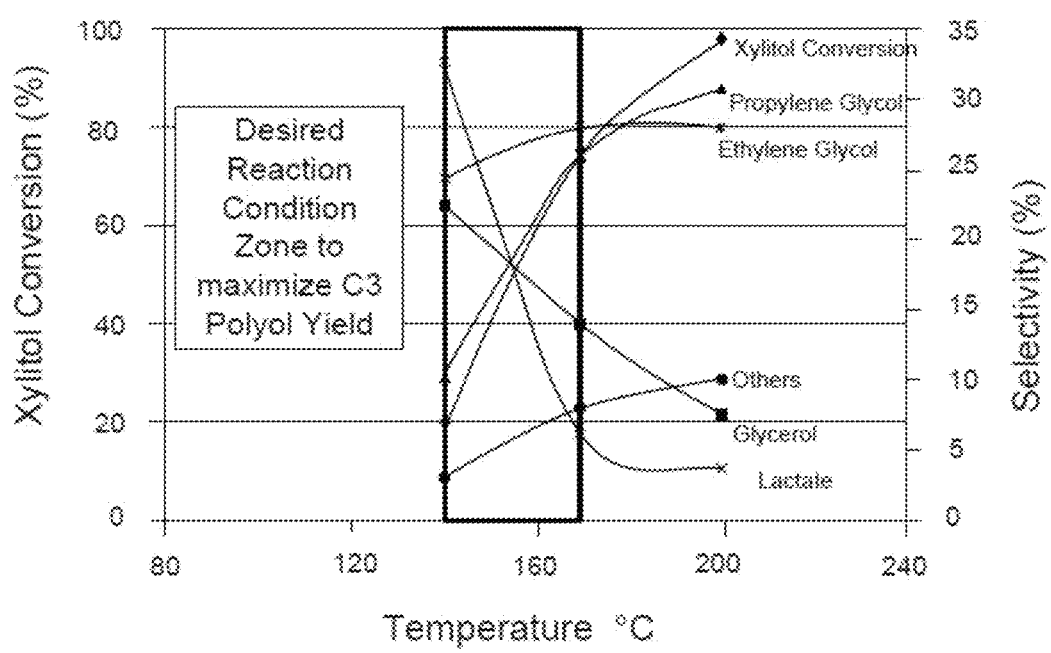
FIG. 3 shows the influence of reaction condition for product distribution of the conversion of sugars to $C_2$, $C_3$ diols and triols, such as ethylene glycol, propylene glycol and glycerol.

For example, hot water extraction of hemicellulose from biomass is a self-catalytic process, autohydrolysis. This mechanism of hydrolysis lies in cleavage of O-acetyl and uronic acid substitutions that result in the formation of acetic and other organic acids, which makes it possible for further hydrolysis of polysaccharides to oligomers and monomers (Niemelä, K., et al, 1999. Characterization of pulping liquors, in: Analytical Methods in Wood Chemistry, Pulping and Papermaking. Springer-Verlag, Berlin). The main degradation pathways of hemicelluloses under acidic conditions liberate xylose, mannose, galactose, glucose, and acetic acid. The temperature and pressure and incubation time can be controlled to avoid the degradation of xylan to furfural (Palmqvist, E., et al, Bioresource Technology (2000) 74, 25-33) and of hexose to 5-hydroxymethylfurfural (HMF). FIG. 3 shows the conversion of xylitol to ethylene glycol, propylene glycol, and glycerol and other products.

The multifunctional catalyst is capable of converting the C5 and/or C6 sugars in a single step to diols and triols. Thus, the there is no need for separation steps or the production of intermediates to produce the diols and triols. Such a method saves both time and resources as compared to methods requiring multiple steps.

The conversion of the C5 and/or C6 sugars to a first product comprising ethylene glycol, propylene glycol, and glycerol in the presence of a multifunctional catalyst is performed in a solvent, such as, for example, water. In one aspect, the method further comprises the step of separating at least a portion of the water from the first product. In one aspect, the concentration of the first product is from about 10 wt % to about 40 wt %, such as, for example, from about 20 wt % to about 35 wt %, in the water after a portion of the water has been separated from the first product.

In one aspect, the multifunctional catalyst comprises one or more metals selected from the group consisting of Cu, Zn, Sn, Ni, Pt, Pd, Ru, and Re, and a support. In one aspect, the support is selected from the group consisting of $Al_2O_3$, $SiO_2$, Carbon, $TiO_2$, and MgO.

Figure 5:
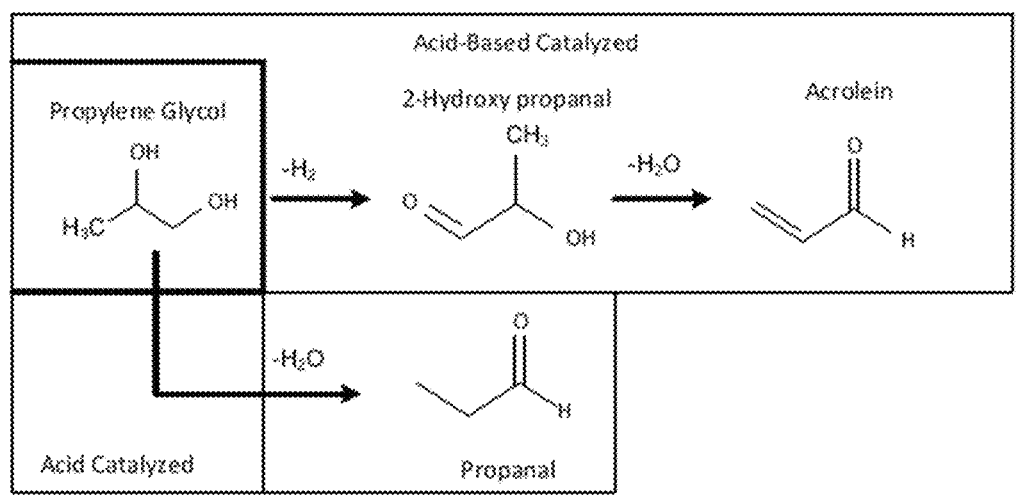
FIG. 5 shows the catalytic reaction pathway for propylene glycol to acrolein and propanal.

In one aspect, the multifunctional catalyst comprises Ni and Cu and the support comprises $Al_2O_3$. The selectivity of various products can be altered by altering the amount of Ni and Cu and the support comprises $Al_2O_3$ as shown in FIG. 5. Cu can serve for C—O cleavage (Dasari, M. A., et al, Applied Catalysis A: General (2005) 281 225-23), Ni for C—C cleavage and hydrogenation and Lewis acid support ($Al_2O_3$) for C—C cleavage and dehydration. Lower amount of copper and nickel over Lewis acid support favors formation of C3 polyols (less cracking), medium nickel and copper favors C2 diols (slight enhanced cracking), whereas even higher Ni and Cu favors formation of alcohols (high degree of both C—C and C—O cleavage with hydrogenation).

In one aspect, the multifunctional catalyst comprises less than 10 wt % of Cu and less than 20 wt % of Ni, and the remainder being $Al_2O_3$. In another aspect, the multifunctional catalyst comprises from about 1 wt % to about 9 wt % of Cu and from about 1 wt % to about 19 wt % of Ni, and the remainder being $Al_2O_3$. Conventional nickel catalyst supported on γ-alumina are unstable due to structural loss under hydrothermal conditions (Ravenelle, R. M., et al, ACS Catalysis (2011) 1, 552-561) making metal sites unavailable. Effect of metal on support structure (Ravenelle, R. M., et al, Chem Cat Chem (2012) 4, 492-494), role of co-adsorbed water on support during C2 and C3 polyol reactions (Copeland, J. R., et al, Langmuir (2013) 29, 581-593) and addition of silica to increase thermal stability has been studied. Furthermore, addition of Cu to Ni catalyst on such supports has known to increase their integrity under hydrothermal conditions (U.S. Pat. No. 5,977,013).

In one aspect, the multifunctional catalyst can further comprise Pt, such as less than 0.5 wt % of Pt, less than 0.3 wt % of Pt, for example, about 0.1 wt % of Pt. The Pt facilitates long term activity and the ability of the catalyst to regenerate.

In one aspect, the first product comprises from about 10 wt % to about 40 wt % of ethylene glycol, from about 10 wt % to about 50 wt % of propylene glycol, and from about 10 wt % to about 50 wt % of glycerol. In one aspect, the first product comprises from about 20 wt % to about 35 wt % of ethylene glycol, from about 30 wt % to about 45 wt % of propylene glycol, and from about 30 wt % to about 45 wt % of glycerol.

In one aspect, at least 95 wt % of the C5 and/or C6 sugars in step a) are converted to the first product comprising ethylene glycol, propylene glycol, and glycerol. In another aspect, at least 98 wt % of the C5 and/or C6 sugars in step a) are converted to the first product comprising ethylene glycol, propylene glycol, and glycerol. In yet another aspect, at least 99 wt % of the C5 and/or C6 sugars in step a) are converted to the first product comprising ethylene glycol, propylene glycol, and glycerol.

In one aspect, the step of converting C5 and/or C6 sugars to a first product comprising ethylene glycol, propylene glycol, and glycerol in the presence of a multifunctional catalyst is performed under mild conditions. For example, the step of converting C5 and/or C6 sugars to a first product comprising ethylene glycol, propylene glycol, and glycerol in the presence of a multifunctional catalyst is performed under mild conditions can be performed at a temperature from about 130° C. to about 200° C., and at a pressure from about 400 psig to about 1000 psig in presence of hydrogen. In another example, the step of converting C5 and/or C6 sugars to a first product comprising ethylene glycol, propylene glycol, and glycerol in the presence of a multifunctional catalyst is performed under mild conditions can be performed at a temperature from about 130° C. to about 180° C., and at a pressure from about 400 psig to about 800 psig in presence of hydrogen.

The use of mild conditions during the conversion of the C5 and/or C6 sugars to the first product allows the multifunctional catalyst to be active for a longer period of time as compared to the same catalyst used under harsher conditions. Desired conversion rates, for example above 95 wt %, of the C5 and/or C6 sugars can be achieved by the method for at least 100 hrs, such as, for example, from 100 hrs to 500 hrs.

In one aspect, the method can further comprise the step of contacting the first product comprising ethylene glycol, propylene glycol, and glycerol with the catalyst composition disclosed herein, thereby producing a second product comprising acrolein and acetaldehyde. In one aspect, the method can further comprise the steps of separating at least a portion of the acetaldehyde from the second product; and converting at least a portion of the acrolein in the second product to acrylonitrile.

In one aspect, the method is performed on an industrial scale. For example, the method can produce at least 30 g/l/hr. such as, for example, at least 45 g/l/hr, of the first product per hour. In another example, the method can produce from about 30 g/l/hr to about 200 g/l/hr of the first product per hour.

Figure 4:
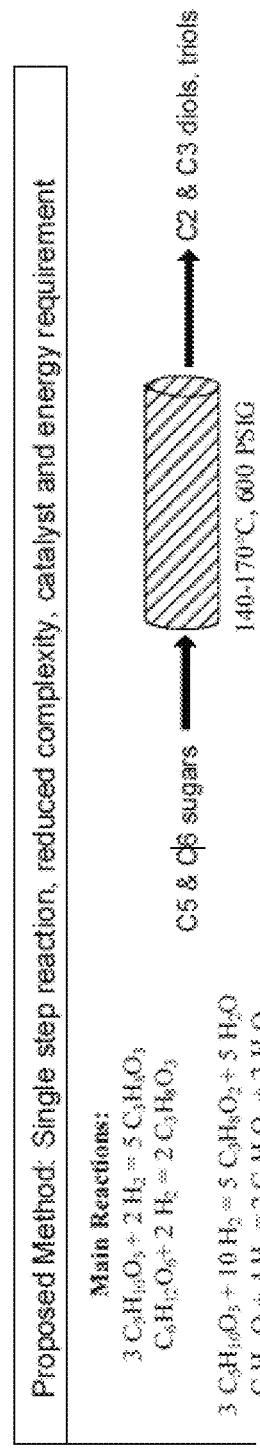
FIG. 4 shows the single step process for hydrocracking reaction for converting sugars to $C_2$, $C_3$ diols and triols, such as ethylene glycol, propylene glycol and glycerol.

A schematic flow of the method disclosed herein is shown in FIG. 4.

II. Production of Acrolein and Hydroxyacetone

In FIG. 1, the second reaction step (Dehydration/dehydrogenation) of the multistep process involves selective conversion of $C_3$ diols (i.e. propylene glycol), triols (i.e. glycerol) to acrolein. In FIG. 1, the product from the first reaction step (hydrocracking of sugar) primarily contains glycerol and propylene glycol at high conversion (100%), selectivity (90%) and stability (>100 hrs). Both propylene glycol and glycerol were tested as feed for the second reaction step to produce acrolein. However, although both propylene glycol and glycerol indeed can be converted to acrolein, the conversion of propylene glycol also produces propanal. It is difficult to separate propanal from acrolein. Accordingly, it can be difficult and expensive to obtain a pure acrolein product if the product contains large amounts of propanal. Thus, it is desired to avoid that propanal and acrolein be produced in the same reaction step.

Furthermore, compared to glycerol, propylene glycol conversion selectivity to acrolein (80% versus 42%) was lower at high conversion (100%).

It was discovered that the overall mechanism of the formation of acrolein from propylene glycol was composed of a number of dehydration and dehydrogenation reactions. Two major intermediates were identified to be responsible for acrolein production, which were allyl alcohol and propanal. However, subsequent production of hydrogen via dehydrogenation further hydrogenated acrolein and reduced its overall selectivity. The produced hydrogen also results in the formation of ethylene glycol, which was found to significantly deactivate the first catalyst disclosed herein. Accordingly, the success of propylene glycol conversion to acrolein will hinge on the effective removal of the produced hydrogen.

As dictated by the product composition from the first reaction step, wherein sugars are converted to ethylene glycol, propylene glycol, and glycerol, propylene glycol constitutes about half of the feed to the following reaction step, wherein about the other half is glycerol. With high acrolein selectivity from glycerol, the overall selectivity for acrolein production in the 2$^{nd}$ reaction step would thus be ~62%. Combined with the potential to produce hydroxyacetone as co-product from glycerol, and the ability to conveniently separate acrolein from hydroxyacetone, the overall efficiency of this process is high. However, such use of mixed feed (propylene glycol and glycerol) also produces propanal and acetaldehyde (low boiling point products) from the propylene glycol and when mixed with acrolein would be difficult to separate and adds impurity to the final product. Accordingly, the method disclosed herein separates propylene glycol from glycerol prior to conversion of the glycerol to the acrolein and co-products. This results in that the product contains no to minimal amounts of propanal, which is undesired in a product mixture with acrolein and increases overall selectivity on carbon basis to 67.5%

The separated propylene glycol can in turn be converted to propanal.

Disclosed herein is a method comprising the step of: a) separating at least a portion of ethylene glycol and propylene glycol from a first product comprising ethylene glycol, propylene glycol, and glycerol, thereby producing a second product comprising glycerol; and b) contacting the second product comprising glycerol with a first catalyst composition disclosed herein, thereby producing a third product comprising acrolein and hydroxyacetone, wherein the first catalyst composition comprises a first catalyst disclosed herein.

In one aspect, the method further comprises the steps of: c) separating at least a portion of the hydroxyacetone from the third product, thereby forming a fourth product comprising acrolein; and; and d) following step c) converting at least a portion of the acrolein in the fourth product to acrylonitrile.

In it known in the art how to convert acrolein to acrylonitrile. For example, acrylonitrile can be produced from acrolein ammoxidation, which is a simultaneous oxidation of an organic group (R) and ammonia, such a mutual reaction results in oxidative condensation product to form R'—CN molecule such as acrylonitrile. Such a reaction is not possible if a separate oxidation of R and ammonia are conducted. Hadley et al (Hadley, D. J., Chemy Ind. (1961) 238) has proposed a two-step reaction mechanism, dehydration due to reaction with ammonia (fast step), and oxidative-dehydration of intermediate (rate limiting step). Therefore, as partial pressure of oxygen increases, the higher surface concentration of oxygen on catalyst leads to higher selectivity to acrylonitrile and acetonitrile (by-product) with net decrease in $CO_2$.

In one aspect, step b) is performed at atmospheric pressure.

In one aspect, the first product is present in a solvent, such as, for example, water.

In one aspect, the second product is present in a solvent, such as, for example, water.

In one aspect, the third product is present in diluent, such as, for example, water. In one aspect, the method can further comprise removing at least a portion of the diluent, thereby concentrating the third product.

The mechanism for the conversion of propylene glycol to acrolein and propanal with various types of catalysts is shown in FIG. 5.

The first product contains high boiling point molecules; propylene glycol (188° C.), ethylene glycol (197.3° C.) and glycerol (290° C.). Propylene glycol and ethylene glycol can be separated from the first product via distillation to form a second product comprising glycerol. In one aspect, at least about 60 wt % of the propylene glycol is separated from the first product. For example, at least about 70 wt %, 80 wt %, 90 wt % or 95 wt % of propylene glycol can be separated from the first product. In another aspect, from about 60 wt % to about 98 wt % of the propylene glycol is separated from the first product. For example, from about 70 wt %, 80 wt %, 90 wt % or 95 wt % to about 98 wt % of the propylene glycol can be separated from the first product.

In one aspect, the second product comprises at least 2 times more glycerol than propylene glycol by weight. For example, the second product can comprise at least 5, 10, 20, 30, 50, of 75 times more glycerol than propylene glycol by weight. In another aspect, the second product comprises from about 2 times to about 90 times more glycerol than propylene glycol by weight. For example, the second product comprises from about 5 times to about 50 times more glycerol than propylene glycol by weight.

In one aspect, from about 50 wt % to about 99 wt % of the glycerol in the second product can be converted to acrolein. For example, from about 60 wt % to about 95 wt % of the glycerol in the second product can be converted to acrolein. In another example, from about 70 wt % to about 95 wt % of the glycerol in the second product can be converted to acrolein.

In one aspect, the third product comprises at least about 50 wt % of acrolein. For example, the third product comprises at least about 60 wt %, 70 wt %, or 80 wt % of acrolein.

In one aspect, the third product comprises from about 50 wt % to about 95 wt % of acrolein and from about 50 wt % to about 5 wt % of hydroxyacetone. For example, third product comprises from about 60 wt % to about 95 wt % of acrolein and from about 40 wt % to about 5 wt % of hydroxyacetone. In another example, third product comprises from about 70 wt % to about 95 wt % of acrolein and from about 30 wt % to about 5 wt % of hydroxyacetone. The third product can be present in a diluent, which is not a part of the third product.

In one aspect, the first product is produced from C5 and/or C6 sugars in a single step using a multifunctional catalyst, as described elsewhere herein. In one aspect, the C5 and/or C6 sugars can be C5 and/or C6 hemicellulose and cellulose derived sugars. The process of producing C5 and/or C6 sugars or C5 and/or C6 hemicellulose and cellulose derived sugars from biomass is also described herein.

It was surprisingly shown that ethylene glycol deactivates the first catalyst composition and first catalyst such that the selectivity and conversion rates of glycerol are significantly decreased. Thus, a method wherein the ethylene glycol is present during conversion of glycerol to acrolein and hydroxyacetone cannot be performed continuously for an extended period of time without losing significant (more than 10% or 20%) selectivity and conversion rates of glycerol. Accordingly, the method disclosed herein avoids this issue by separating ethylene glycol from the first product, thereby minimizing its presence during the conversion of glycerol to acrolein and hydroxyacetone. Therefore, the method disclosed herein can be performed continuously for an extended time without significant (less than 10%) loss in selectivity and conversion rate of glycerol to acrolein and hydroxyacetone.

In one aspect, the method comprising the step of: a) separating at least a portion of ethylene glycol and propylene glycol from a first product comprising ethylene glycol, propylene glycol, and glycerol, thereby producing a second product comprising glycerol; and b) contacting the second product comprising glycerol with a first catalyst composition disclosed herein, thereby producing a third product comprising acrolein and hydroxyacetone, wherein the first catalyst composition comprises a first catalyst disclosed herein can be performed for at least 5 hours without losing more than 10% of the conversion rate of the second product to the third product. In one aspect, the method comprising the step of: a) separating at least a portion of ethylene glycol and propylene glycol from a first product comprising ethylene glycol, propylene glycol, and glycerol, thereby producing a second product comprising glycerol; and b) contacting the second product comprising glycerol with a first catalyst composition disclosed herein, thereby producing a third product comprising acrolein and hydroxyacetone, wherein the first catalyst composition comprises a first catalyst disclosed herein can be performed for at least 24 hours without losing more than 10% of the conversion rate of the first product to the second product. In one aspect, the method comprising the step of: a) separating at least a portion of ethylene glycol and propylene glycol from a first product comprising ethylene glycol, propylene glycol, and glycerol, thereby producing a second product comprising glycerol; and b) contacting the second product comprising glycerol with a first catalyst composition disclosed herein, thereby producing a third product comprising acrolein and hydroxyacetone, wherein the first catalyst composition comprises a first catalyst disclosed herein can be performed from about 5 hours to about 50 hours without losing more than 10% of the conversion rate of the first product to the second product.

In one aspect, the method is performed on an industrial scale. For example, the method can produce at least 75 g/l of the third product per hour.

A schematic flow of the method disclosed herein is shown in FIG. 1.

In one aspect, the method further comprises contacting at least a portion of the separated propylene glycol with a second catalyst composition disclosed herein, thereby producing propanal, wherein the second catalyst composition comprises a second catalyst disclosed herein.

In one aspect, the second catalyst composition converts at least about 60 wt % of the separated propylene glycol to propanal. For example, the second catalyst composition can convert at least about 70 wt %, 80 wt %, or 90 wt % of the separated propylene glycol to propanal. In another aspect, the second catalyst composition converts from about 60 wt % to about 98 wt % of the separated propylene glycol to propanal. For example, the second catalyst composition can convert from about 70 wt %, 80 wt %, or 90 wt % to about 98 wt % of the separated propylene glycol to propanal.

In one aspect, the method further comprises converting the propanal to acrolein.

Also disclosed herein is a method comprising the step of: a) contacting propylene glycol with a third catalyst composition disclosed herein, thereby producing propanal, wherein the third catalyst composition comprises a third catalyst disclosed herein.

In one aspect, the third catalyst composition converts at least about 60 wt % of the propylene glycol to propanal. For example, the third catalyst composition can convert at least about 70 wt %, 80 wt %, or 90 wt % of the propylene glycol to propanal. In another aspect, the third catalyst composition converts from about 60 wt % to about 98 wt % of the propylene glycol to propanal. For example, the third catalyst composition can convert from about 70 wt %, 80 wt %, or 90 wt % to about 98 wt % of the propylene glycol to propanal.

In one aspect, the method further comprises converting the propanal to acrolein.

3. Aspects

In view of the disclosure herein below are described certain more particularly described aspects of the inventions. These particularly recited aspects should not however be interpreted to have any limiting effect on any different claims containing different or more general teachings described herein, or that the "particular" aspects are somehow limited in some way other than the inherent meanings of the language and formulas literally used therein.

Aspect 1: A method comprising the steps of: a) separating at least a portion of ethylene glycol and propylene glycol from a first product comprising ethylene glycol, propylene glycol, and glycerol, thereby producing a second product comprising glycerol; and b) contacting the second product comprising glycerol with a first catalyst composition, thereby producing a third product comprising acrolein and hydroxyacetone, wherein the first catalyst composition comprises a first catalyst having the formula:

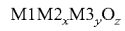

$$M1M2_xM3_yO_z$$

wherein M1 is a metal promoting C—O cleavage,
wherein M2 is a metal with acid sites promoting dehydration,
wherein M3 is an amphoteric catalyst support, with acid and base sites, promoting selective dehydration in conjunction with M1,
wherein x is a molar ratio from about 0.25 to about 4,
wherein y is a molar ratio from about 0.25 to about 4,
wherein z is the total amount of oxygen bound to M1, M2, and M3, and corresponds to the sum of the oxidation states of M1, M2, and M3.

Aspect 2: The method of aspect 1, wherein the method further comprises the steps of: c) separating at least a portion of the hydroxyacetone from the third product, thereby forming a fourth product comprising acrolein; and d) following step c) converting at least a portion of the acrolein in the fourth product to acrylonitrile.

Aspect 3: The method of aspects 1 or 2, wherein the method further comprises prior to step a), in a single step, converting C5 and/or C6 sugars to the first product comprising ethylene glycol, propylene glycol, and glycerol in the presence of a multifunctional catalyst.

Aspect 4: The method of any one of aspects 1-3, wherein the method further comprises contacting at least a portion of the separated propylene glycol with a second catalyst composition, thereby producing propanal, wherein the second catalyst composition comprises a second catalyst having the formula:

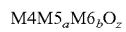

$$M4M5_aM6_bO_z$$

wherein M4 is a metal with acid sites promoting dehydration,
wherein M5 is an amphoteric catalyst support, with acid and base sites, promoting selective dehydration in conjunction with M6 when present,
wherein M6 is a metal promoting C—O cleavage,
wherein a is a molar ratio from about 0.25 to about 4,
wherein b is a molar ratio from 0 to about 4,
wherein z is the total amount of oxygen bound to M4, M5, and M6, and corresponds to the sum of the oxidation states of M4, M5, and M6.

Aspect 5: The method of any one of aspects 1-4, wherein M1 is selected from the group consisting of Cu, Zn, and Sn.

Aspect 6: The method of any one of aspects 1-5, wherein M2 is selected from the group consisting of W, Fe, P, and, a zeolite.

Aspect 7: The method of any one of aspects 1-6, wherein M3 is selected from the group consisting of Zr, Al, Si, Mg, Ti, La, and Ce.

Aspect 8: The method of any one of aspects 1-7, wherein M1 is Cu.

Aspect 9: The method of any one of aspects 1-8, wherein M2 is W.

Aspect 10: The method of any one of aspects 1-9, wherein M3 is Zr.

Aspect 11: The method of any one of aspects 1-10, wherein the catalyst has the formula $CuOWO_3ZrO_2$, or $CuOWO_3TiO_2$, or $CuOWO_3SiO_2$.

Aspect 12: The method of any one of aspects 3-11, wherein the C5 and/or C6 sugars is C5 and/or C6 hemicellulose and cellulose derived sugars.

Aspect 13: The method of any one of aspects 3-12, wherein the multifunctional catalyst comprises one or more metals selected from the group consisting of Cu, Zn, Sn, Ni, Pt, Pd, Ru, and Re, and a support.

Aspect 14: The method of aspect 15, wherein the support is selected from the group consisting of $Al_2O_3$, $SiO_2$, carbon, $TiO_2$, and MgO.

Aspect 15: The method of any one of aspects 1-14, wherein the method is performed continuously for at least 5 hours.

Aspect 16: The method of any one of aspects 1-15, wherein at least 60 wt % of the propylene glycol is separated from the first product.

Aspect 17: The method of any one of aspects 1-16, wherein the third product comprises at least 50 wt % of acrolein.

Aspect 18: The method of any one of aspects 1-18, wherein the second product comprises at least 2 times more glycerol than propylene glycol by weight.

Aspect 19: A method comprising the step of: a) contacting propylene glycol with a third catalyst composition, thereby producing propanal, wherein the third catalyst composition consisting essentially of a third catalyst having the formula:

$$M4M5_aO_z$$

wherein M4 is a metal with acid sites promoting dehydration,
wherein M5 is an amphoteric catalyst support, with acid and base sites, promoting selective dehydration,
wherein a is a molar ratio from about 0.25 to about 4,
wherein z is the total amount of oxygen bound to M4 and M5, and corresponds to the sum of the oxidation states of M4 and M5.

Aspect 20: The method of aspect 19, wherein M4 is selected from the group consisting of W, Fe, P, and, a zeolite, and M5 is selected from the group consisting of Zr, Al, Si, Mg, Ti, La, and Ce.

4. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. The Examples are provided herein to illustrate the invention, and should not be construed as limiting the invention in any way.

1. Experimental Parameters and Testing of Catalysts

Preparation of $CuOWO_3ZrO_2$: A Tungsten Hexachloride Solution in Ethanol (0.056 g/ml of solution) was prepared (other salts of tungsten such ammonium paratungstate (APT) and ammonium metatungstate (AMT) dissolved in water were also used). It is noted that other tungsten salts may also be used in this process. $ZrO_2$ was obtained from Alfa Aesar (catalog number 43815) with a surface area of 90 $m^2/g$. This was crushed to the required size (−20, +35 mesh) and the required amount of Tungsten Hexachloride solution for 20 wt % resultant $WO_3$ was added (61.6 ml, the salt has poor solubility and thus excess solution was added), along with 10 ml of water to achieve better dissolution and retrieve traces of salt. The solution was impregnated on crushed $ZrO_2$ and allowed to dry at room temperature for 4 to 5 hrs. A second solution of Copper nitrate hexahydrate (0.043 g/ml) was prepared; this solution was impregnated on top of previously obtained tungsten hexachloride on $ZrO_2$ sample. The sample was allowed to dry at 100° C. overnight. Dried sample was calcined in a high temperature oven under air using following program, room temperature to 100° C. at 1° C./min and held at 110° C. for 1 hour, then 110° C. to 450° C. at 5° C./min, and held at 450° C. for 3 hours.

Preparation of $WO_3SiO_2$ and $CuOWO_3SiO_2$ catalysts: A 75 ml aqueous solution of ammonium paratungstate (APT) salt (0.014 g/ml of solution) was prepared at 80° C. under continuous stirring for 4-6 hours. An excess volume and an elevated temperature were used as this salt is poorly soluble in water. 4 g of $SiO_2$, obtained from Degussa (Aerosil® 200, catalog number 132138) as fumed silica, with a surface area of 200 $m^2/g$, was subsequently added to the APT solution. The excess water was evaporated by overnight stirring at 60° C. The sample was then allowed to dry at 100° C. over night. The dried sample was calcined in a high temperature oven under static air using following program: room temperature to 100° C. at 1° C./min and held at 110° C. for 1 hour, then 110° C. to 450° C. at 2.5° C./min and held at 450° C. for 4 hours. The prepared catalyst contained 20 wt % $WO_3$.

For the preparation of $CuOWO_3SiO_2$ catalyst, 0.99 g of copper nitrate ($Cu(NO_3)_2.3H_2O$) salt dissolved in 10 ml water was additionally impregnated to the calcined $WO_3SiO_2$ catalyst via incipient wetness impregnation. The resulting sample was dried at 100° C. over night and then calcined using the same high temperature calcination protocol as the $WO_3SiO_2$ sample. The CuO loading on the resulting catalyst was 5 wt %. After calcination both the catalysts were pelletized and sieved to (−20, +35 mesh).

2. Experimental Parameters and Testing of Catalysts for Glycerol Conversion to Acrolein WO3/ZrO2, $CuOWO_3ZrO_2$ and WO3/SiO2 catalyst were tested for the conversion of glycerol to acrolein. 5 wt % glycerol was used as a reactant and a co flow of $N_2$ of 50 SCCM This reaction was conducted in fixed bed reactor. The catalyst was loaded in the center of heated zone, with inert low surface glass beads as filler material on top and bottom of reactor. At the bottom of reactor a 5 micron metal grid was used as support for catalyst material. At the inlet of reactor, feed was preheated to desired temperature. The gas phase reaction was studied at 280° C. and 1 atm using $WO_3/ZrO_2$, $CuO/WO_3/ZrO_2$, and $WO_3/SiO_2$ as dehydrating catalysts, with a flow of 1 g/hr and 1 grams of each catalyst for a WHSV of 1/hr. The gas effluent was connected to an online GC-FID which was pre-calibrated for acrolein, by-products and feed component. The presence of acrolein in the product was confirmed using a standard on GC-FID and GC-MS.

TABLE 1

| Catalyst | $WO_3/ZrO_2$ | $CuO/WO_3/ZrO_2$ | $WO_3/SiO_2$ |
|---|---|---|---|
| Temperature - °C. | 280 | 280 | 280 |
| Pressure - psig | 14.7 | 14.7 | 14.7 |
| Glycerol conversion - % | 100% | 100% | 100% |
| Selectivity to Acrolein - % | 82% | 35% | 71% to 82% |

As shown in Table 1, a $CuO/WO_3/ZrO_2$ have intermediate selectivity and $WO_3/SiO_2$ catalyst have comparable selectivity for the production of acrolein from glycerol as compared to a $WO_3/ZrO_2$ catalyst.

Figure 14:
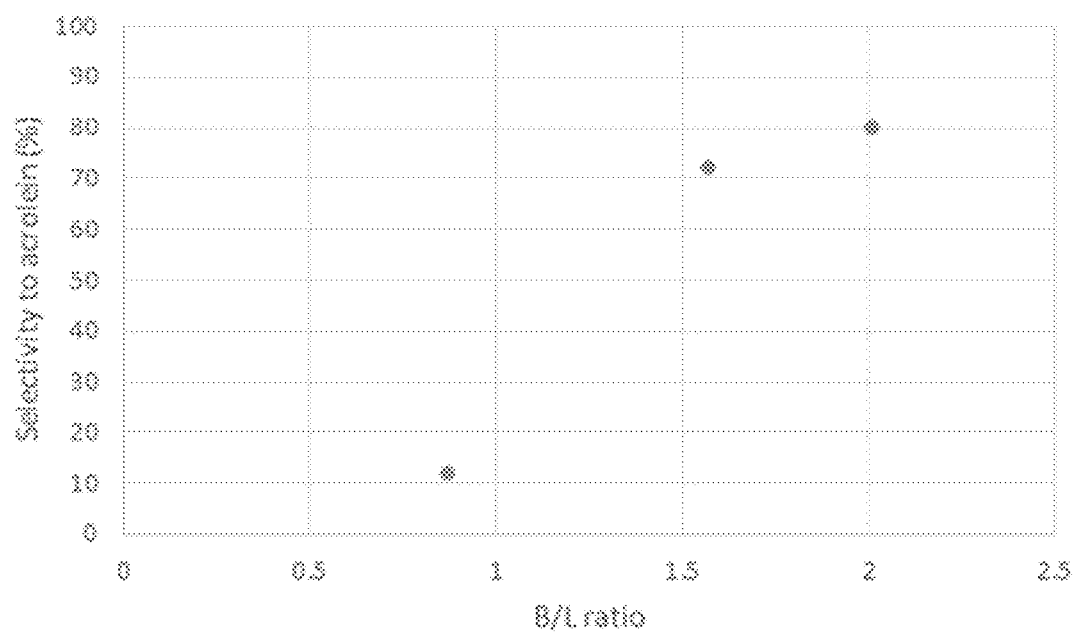
FIG. 14 shows the effect of Bronsted-to-Lewis (B/L) site ration on acrolein selectivity.

The role of acid sites in the catalyst: In order to determine effect of acid sites in the catalyst, two types of measurements were conducted—total acidity using $NH_3$-TPD and Bronsted-to-Lewis acidity ratio using FTIR-Pyridine. The role of acidity was determined, as follows:

1. Table 2 shows evidence of high Bronsted to Lewis acid site ratio (B/L) in 20-$WO_3/SiO_2$ (APT salt) similar to the 10.45-$WO_3/ZrO_2$ (APT salt) catalyst;
2. B/L ratio correlates with selectivity of acrolein, as shown in FIG. 14;
3. AMT catalyst have lower total acid site density and as well as B/L ratio. Therefore, most AMT catalysts performed poorly as compared to APT salt catalyst as described herein;
4. The addition of CuO increased the total acidity of the catalyst and resulted in the formation of hydroxyacetone and lower selectivity to acrolein, see Table 2.

TABLE 2

| Catalyst | Total acidity (mmoles/g) | B/L ratio |
|---|---|---|
| 10.45-$WO_3/ZrO_2$ (APT) | — | 2.01 |
| 11-$WO_3/ZrO_2$ (AMT) | 0.145 | 0.87 |
| 5-CuO/11-$WO_3/ZrO_2$ (AMT) | 0.463 | — |
| 20-$WO_3/SiO_2$ (APT) | 0.117 | 1.57 |
| 5-CuO/20-$WO_3/SiO_2$ (APT) | 0.250 | — |

Role of Support and Surface Area:

Two types of support were studied—i) $ZrO_2$, an amphoteric support with both acid and base sites; and ii) $SiO_2$, a weak acid with no basic sites.

Table 3 shows that the net catalyst surface area for $WO_3/SiO_2$ catalyst is significantly higher than the $ZrO_2$ supported catalyst. Both catalysts show a high initial activity (100% conversion). However, the $SiO_2$ catalyst shows a much longer life time under the tested conditions.

TABLE 3

| Catalyst | Support surface area ($m^2$/gm) | Catalyst surface area after $WO_3$ deposition ($m^2$/gram) |
|---|---|---|
| 10.45 wt % $WO_3/ZrO_2$ | 90 | 37 |
| 20 wt % $WO_3/SiO_2$ | 250 | 150 |

Lifetime of Catalyst:

Table 4 shows that $WO_3/SiO_2$ catalyst has longer life (51 hours v. 15-20 hours) as compared to $WO_3/ZrO_2$ catalyst.

Since $ZrO_2$ is a known amphoteric oxide, 10.45-$WO_3/ZrO_2$ is expected to retain significant amount of basic sites. Surprisingly, 20-$WO_3/SiO_2$ does not retain such significant basicity as $SiO_2$ is inherently neutral and with introduction of $WO_3$ attains a handful of acid sites and but no basic sites. It is possible, that due to lack of $WO_3$ loading on $ZrO_2$ support, which is conducted to induce weak acid sites, basic sites are still active and leading to secondary dehydration/condensation reactions responsible for catalyst deactivation.

Co-feeding the reaction with air improved acrolein selectivity for the 20-$WO_3/SiO_2$ catalysts to 82% (from 71% without air) (see Table 1).

Although the selectivity to acrolein obtained from these two catalysts were similar (see Table 4, the lifetime of the acidic 20-$WO_3/SiO_2$ catalyst was higher than the amphoteric 10.45-$WO_3/ZrO_2$ catalyst.

TABLE 4

| Catalyst | Composition | Feed Conversion Glycerol (%) | Selectivity to acrolein (%) | Catalyst life (hrs) |
|---|---|---|---|---|
| 1 | 10.45 wt % $WO_3/ZrO_2$ | 100 | 80 | 15-20 |
| 2 | 20 wt % $WO_3/SiO_2$ | 100 | 71 to 82 | ~51 |

Both the $WO_3SiO2$ and $CuOWO_3ZrO_2$ catalysts were also tested for the conversion of propylene glycol. 5 wt % propylene glycol with a co flow of $N_2$ of 50 SCCM was used as reactant and the reaction was conducted in a fixed bed reactor. The catalyst was loaded in the center of heated zone, with inert low surface glass beads as filler material on top and bottom of reactor. At the bottom of reactor a 5 micron metal grid was used as support for catalyst material. At the inlet of reactor, feed was preheated to desired temperature. The gas phase reaction was studied at 280° C. and 1 atm with a weight hourly space velocity (WHSV) of 1/hr using 1 g catalyst. At these conditions, $WO_3SiO_2$ catalyst underwent dehydration and dehydrogenation reactions which resulted in the formation of propanal, acrolein and ethylene glycol (EG). The results using this catalyst appear in Table 5, FIG. 2 and FIG. 6. On the other hand, on the $CuOWO_3SiO_2$ catalyst only dehydration mechanism was active which resulted in very selective production of propanal (no acrolein or EG). The results have been listed in Table 5 and plotted in FIG. 6. The gas effluent was connected to an online GC-FID which was pre-calibrated for acrolein and feed component. The presence of listed products were confirmed using a standard on GC-FID and GC-MS.

TABLE 5

| Catalyst | $WO_3/SiO_2$ | $CuO/WO_3/SiO_2$ |
|---|---|---|
| Temperature - °C. | 280 | 280 |
| Pressure - psig | 14.7 | 14.7 |
| Propylene glycol conversion - % | 100%* | 100% |
| Selectivity: | | |
| Acrolein - % | 11 | 0 |
| Propanal - % | 33 | 82 |
| EG - % | 30 | 1 |

*Conversion dropped to 0 within 8 h due to catalyst deactivation

2. Experimental Parameters and Testing of Catalysts for Sugar Conversion to Glycols and Glycerol Catalyst for conversion of sugar to glycols was prepared using following methods and materials: catalyst 1) 0.1 wt % Pt/10 wt % Ni/$Al_2O_3$—Nickel Hexhydrate salt was dissolved in water for a resultant concentration of 0.04036 grams of Ni/gram of solution. 0.25 grams of Tetraamineplatinum (II) nitrate solution was added to this solution. Commercial Alumina obtained from Alfa Aesar (catalog number 43855) with a surface area of 220 $m^2$/g and pore size of 70 Å was used. This support was crushed and sieved to (−20, +35 mesh). Salt solution was impregnated on the solid catalyst support to obtain desired metal concentration ranging from 1 to 20 wt % of metal (Ni) and 0.1 wt % of Pt. The sample was allowed to dry at room temperature for 3 hrs and then at 60° C. on a hot plate overnight. Dried sample was calcined under air in a conventional high temperature oven using the following program. Room temperature to 100° C. in 1.5 hours, held at 100° C. for 1 hour, 100 to 120° C. in 30 minutes, held at 120° C. for 1 hour, 120 to 450° C. at 10° C./min and held at 450° C. for 3 hours.

Catalyst 2): For a 0.1 wt % Pt/10 wt % Ni/10 wt % Cu/Al$_2$O$_3$ catalyst—Nickel Hexhydrate salt was dissolved in water for a resultant concentration of 0.04036 grams of Ni/gram of solution. 0.25 grams of Tetraamineplatinum (II) nitrate solution was added to this solution. Commercial Alumina obtained from Alfa Aesar (catalog number 43855) with a surface area of 220 m2/g and pore size of 70 Å was used. This support was crushed and sieved to (−20, +35 mesh). Salt solution was impregnated on the solid catalyst support to obtain desired metal concentration ranging from 1 to 20 wt % of metal (Ni) and 0.1 wt % of Pt. The sample was allowed to dry at room temperature for 3 hrs and then at 60° C. on a hot plate overnight. Similarly, copper solution was prepared using Copper nitrate hexahydrate in water for a concentration of (0.0789 grams of copper/gram of solution). This solution was impregnated on top of the obtained sample, dried at room temp for 3 hours and then at 60° C. overnight.

Figure 10:
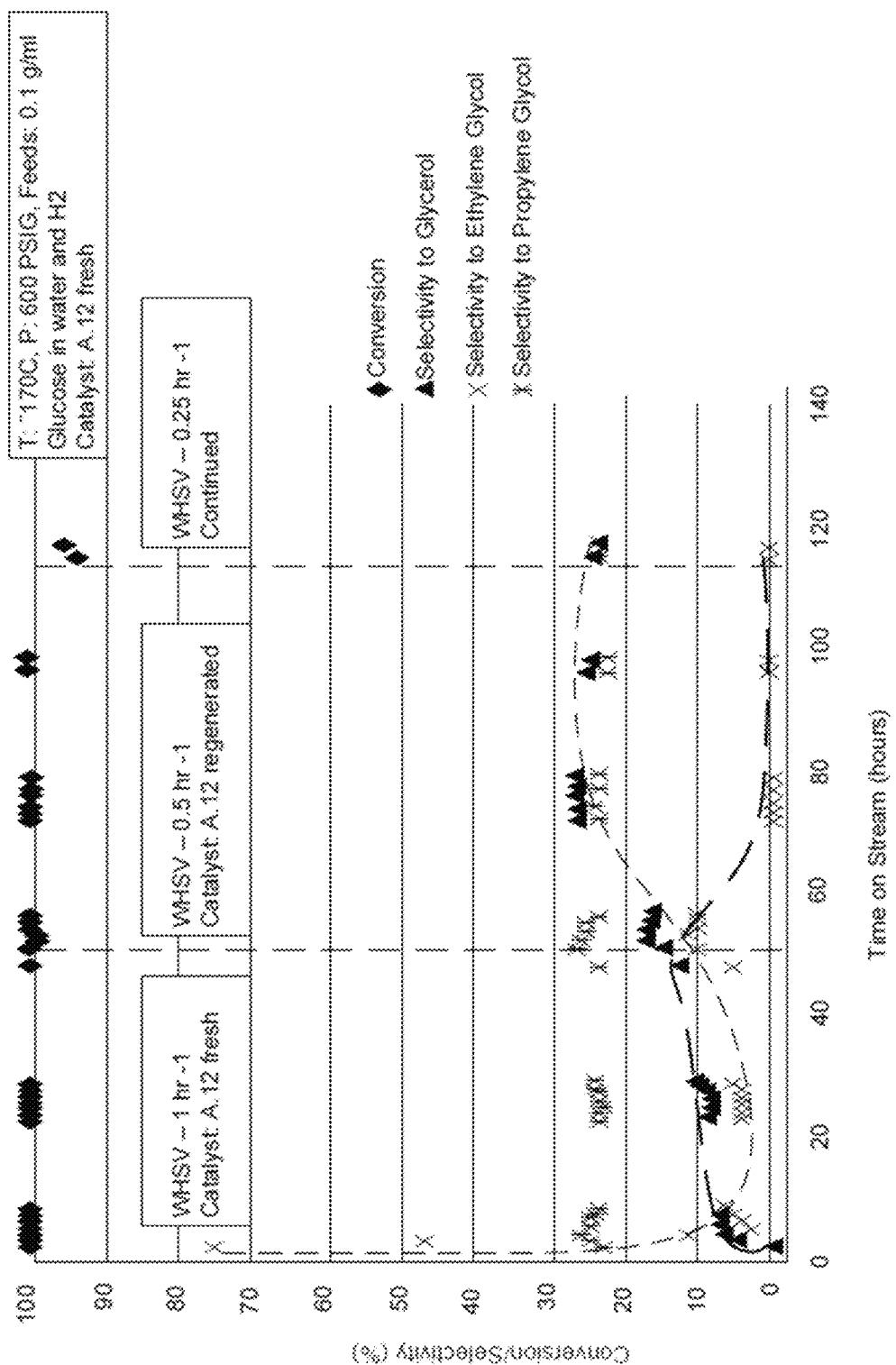
FIG. 10 shows the stability as a function of time and reaction conditions for catalyst 3).
Figure 11:
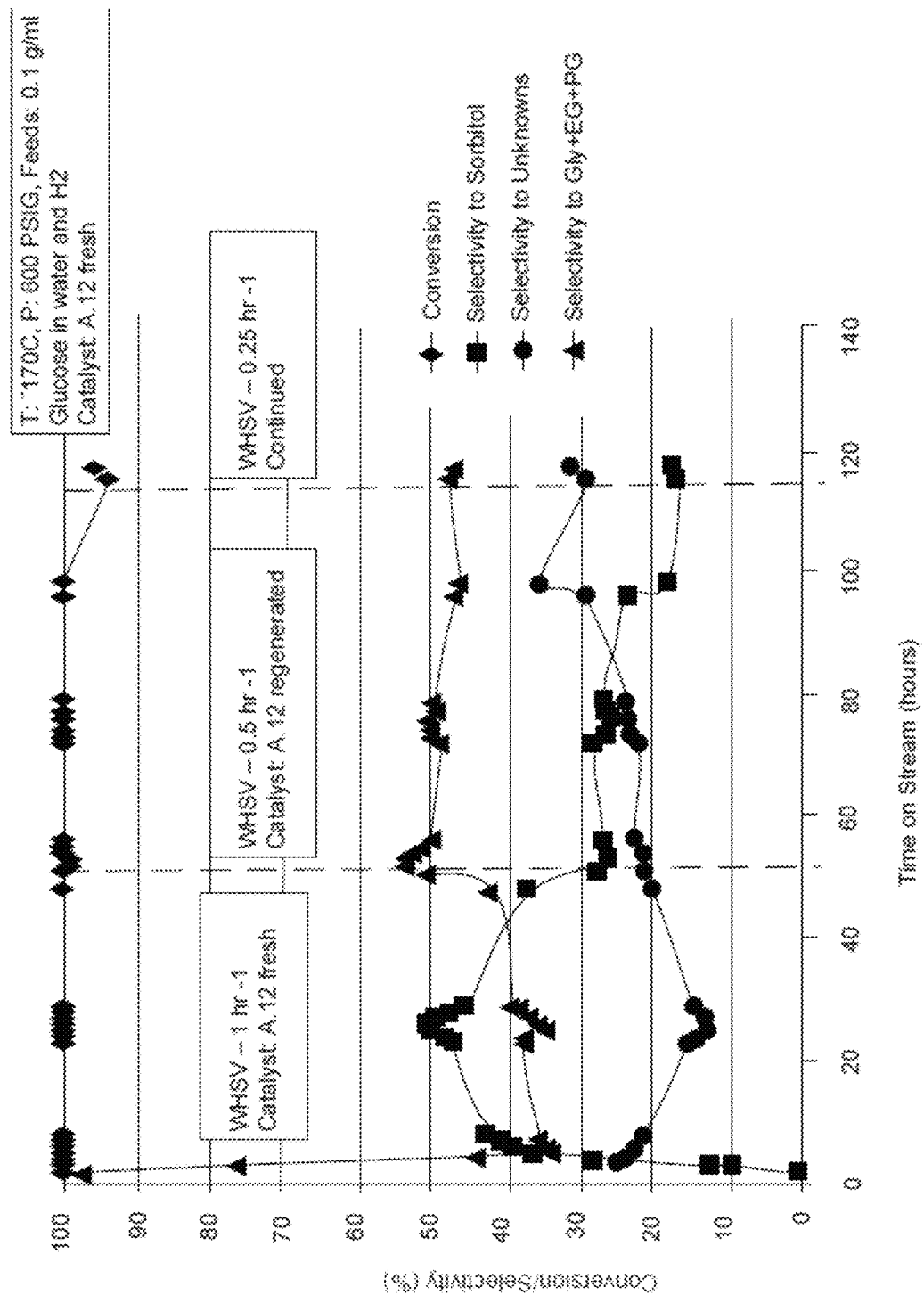
FIG. 11 shows the selectivity as a function of time and reaction conditions for catalyst 3).

Catalyst 3): For a 0.1 wt % Pt/10 wt % Nil 10 wt % Cu/Al$_2$O$_3$ catalyst (Catalyst A. 12, as shown in FIGS. 10 and 11)—Copper Nitrate trihydrate salt was dissolved in water for a resultant concentration of 0.078 grams of Cu/gram of solution. Commercial Alumina obtained from Alfa Aesar (catalog number 43855) with a surface area of 220 m$^2$/g and pore size of 70 Å was used. This support was crushed and sieved to (−20, +35 mesh). Salt solution was impregnated on the solid catalyst support to obtain desired metal concentration ranging from 1 to 20 wt % of metal (Cu). The sample was allowed to dry at room temperature for 3 hrs and then at 60° C. on a hot plate overnight. Dried sample was calcined under air in a conventional high temperature oven using the following program. The temperature was increased from room temperature to 60° C. at a rate of 12° C./min and held at 60° C. for 5 minutes. The temperature was increased from 60° C. to 100° C. at 14° C./min, and held at 100° C. for 1 hour. The temperature was then increased from 100° C. to 120° C. at 7° C./min, and held at 120° C. for 1.5 hours. The temperature was then increased from 120° C. to 450° C. at 10° C./min and held at 450° C. for 3 hours. Following calcination, the catalyst sample was allowed to cool down to room temperature. A second metal impregnation was then conducted, Nickel solution was prepared using nickel nitrate hexahydrate in water for a concentration of (0.05 grams of nickel/gram of solution). 0.25 grams of Tetraamineplatinum (II) nitrate solution was added to this solution. Resultant salt solution was impregnated on the calcined sample to obtain desired metal concentration ranging from 1 to 20 wt % of metal (Ni) and 0.1 wt % of Pt. Sample was dried at room temp for 3 hours and then at 60° C. overnight. The dried sample was calcined under air in a conventional high temperature oven using the following program. The temperature was increased from room temperature to 60° C. at a rate of 12° C./min and held at 60° C. for 5 minutes. The temperature was increased from 60° C. to 100° C. at 14° C./min, and held at 100° C. for 1 hour. The temperature was then increased from 100° C. to 120° C. at 7° C./min, and held at 120° C. for 1.5 hours. The temperature was then increased from 120° C. to 450° C. at 10° C./min and held at 450° C. for 3 hours. Following calcination, catalyst sample was allowed to cool down to room temperature and stored for testing.

Catalyst Testing: The Pt/Ni/Al$_2$O$_3$ sample was tested as a catalyst for the conversion of glucose to ethylene glycol, propylene glycol and glycerol. 10 wt % glucose in water was used as feed with Hydrogen as co feed at 50 SCCM. The reaction was conducted in a fixed bed reactor, in trickle flow, top down approach. Prior to reactor entrance a preheating zone was included to heat feed to desired temperature. The catalyst was filled in the center of reactor with inert glass beads as filler materials on top and bottom of the reactor. A 5 micron metal frit was used at the bottom of reactor to secure catalyst in place. 5 grams of catalyst was loaded with a flow rate of liquid 10 wt % glucose in water varying from 2.5 to 10 ml/hr. The temperature was varied from 150 to 200 C and pressure from 450 to 750 PSIG.

Figure 7:
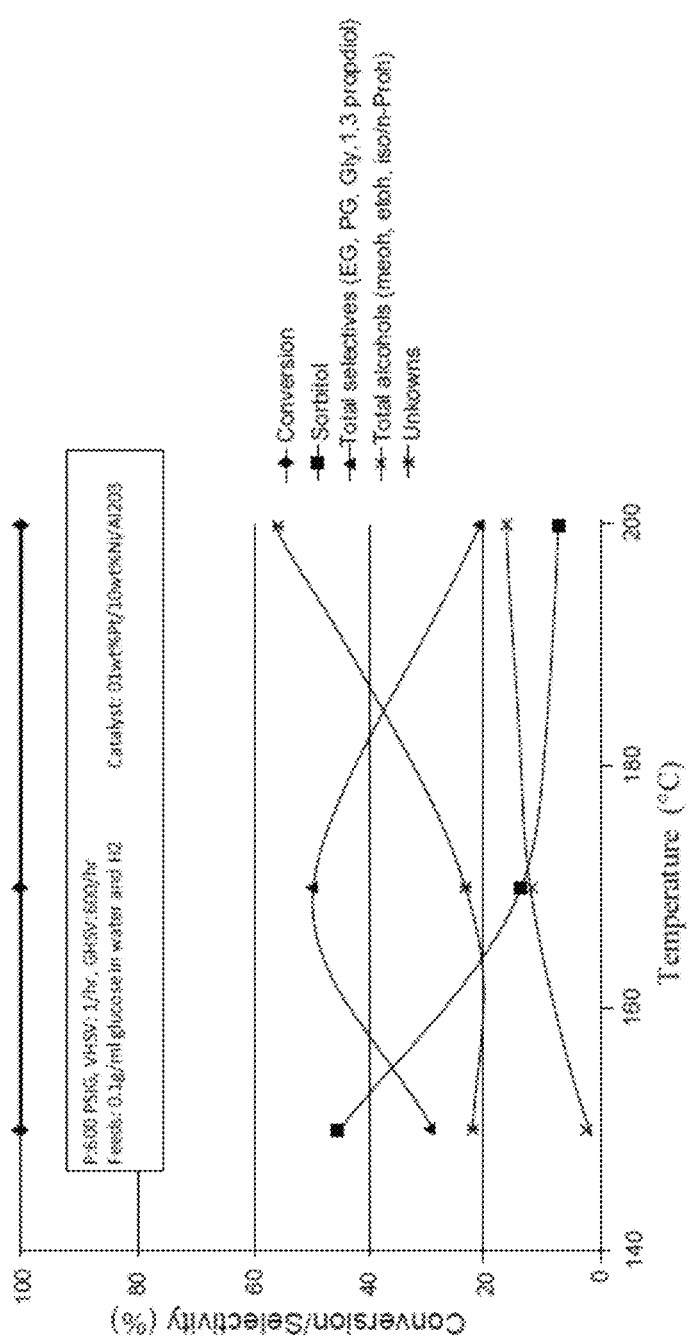
FIG. 7 shows the glucose conversion to glycols as a function of temperature for catalyst 1).

The results of the experiments described above are shown in FIGS. 7-9 are for catalyst 1) described above. FIG. 7 shows the glucose conversion to glycols as a function of temperature for catalyst 1). The data in FIG. 7 was produced using the following conditions: WHSV—1/hr, GHSV—600/hr, Pressure 600 PSIG, Feed of 10 wt % glucose and H$_2$. The selectivity for the production of ethylene glycol, propylene glycol, and glycerol was highest between 160° C. and 180° C.

Figure 8:
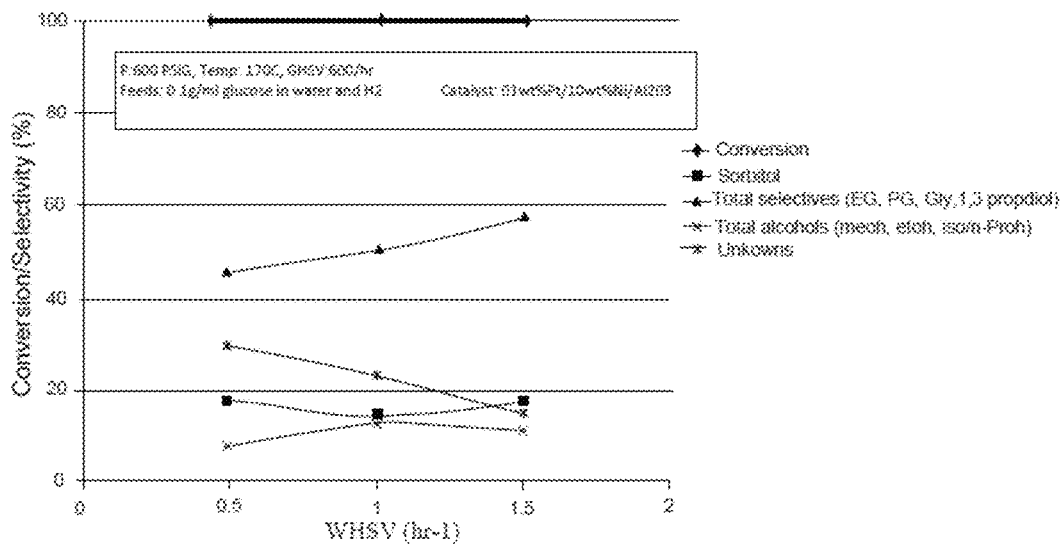
FIG. 8 shows the glucose conversion to glycols as a function of WHSV for catalyst 1).

FIG. 8 shows the glucose conversion to glycols as a function of WHSV for catalyst 1). The data in FIG. 8 was produced using the following conditions: GHSV—600/hr, Pressure 600 PSIG, Temperature 170° C. Feed of 10 wt % glucose and H$_2$. The selectivity for the production of ethylene glycol, propylene glycol, and glycerol was highest at a WHSV of 1.5/hr.

Figure 9:
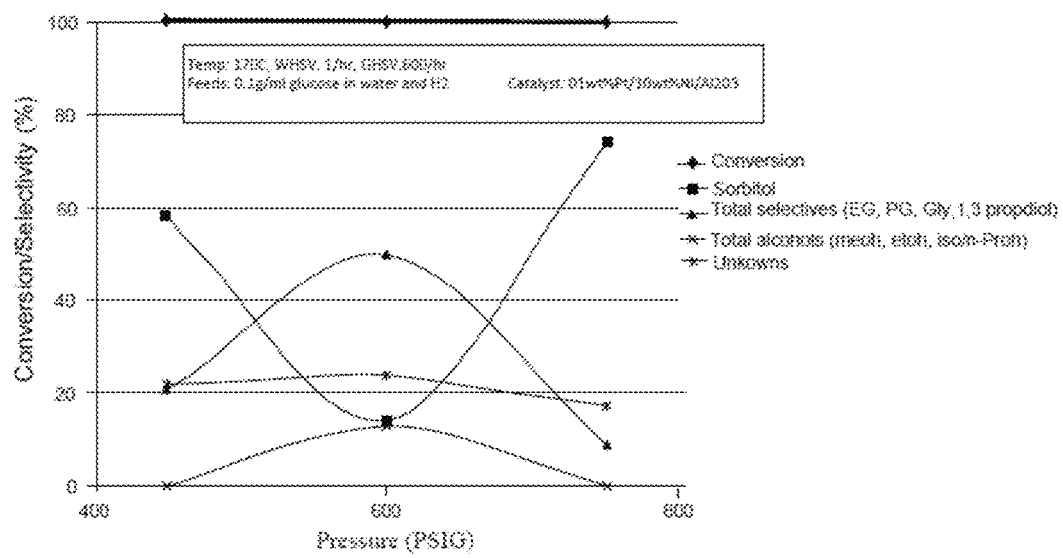
FIG. 9 shows the glucose conversion to glycols as a function of pressure for catalyst 1).

FIG. 9 shows the glucose conversion to glycols as a function of pressure for catalyst 1). The data in FIG. 9 was produced using the following conditions: WHSV—1/hr, GHSV—600/hr, Temperature 170° C. Feed of 10 wt % glucose and H$_2$. The selectivity for the production of ethylene glycol, propylene glycol, and glycerol was highest at a pressure between 550 and 650 psig.

FIG. 10 shows that Catalyst 3) was stable for more than 100 hours with a 100% conversion in a reaction under the following conditions: WHSV—1/hr (0 to about 50 hrs), 0.5 hr-1 (from about 50 hrs to about 115 hrs), 0.25 hr-1 (from about 115 hrs to about 120 hrs), GHSV—600/hr, Temperature 170° C. Feed of 10 wt % glucose in water and H$_2$. Pressure 600 psig. FIG. 10 also shows the selectivity for the production of ethylene glycol, propylene glycol, and glycerol over the course of the reaction.

FIG. 11 shows the selectivity of Catalyst 3) for the production of ethylene glycol, propylene glycol, and glycerol, as compared to the selectivity of sorbitol and unknowns over the course of the reaction as described for FIG. 10. The selectivity for ethylene glycol, propylene glycol, and glycerol, as compared to the selectivity of sorbitol and unknowns was stable over the course of the reaction.

3. First Catalyst Deactivation by Ethylene Glycol

Figure 2:
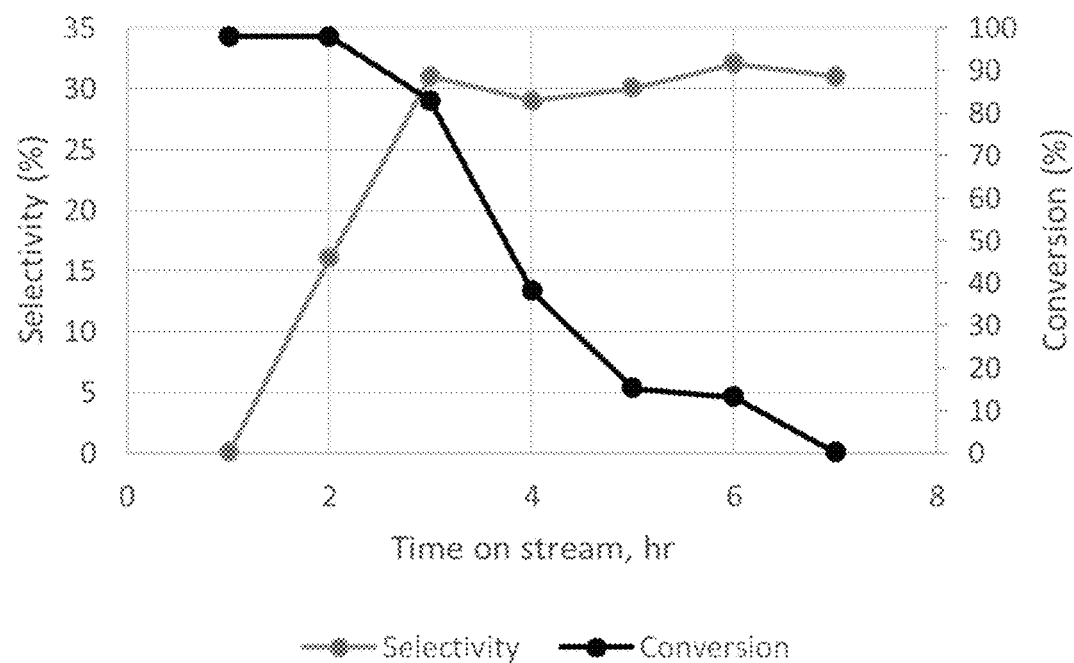
FIG. 2 shows the conversion of propylene glycol using a 20-$WO_3$/$SiO_2$ catalyst.

Polyols (diols and triols) were produced selectively from biomass derived sugar as described herein at high conversion. However, as shown in FIG. 2, the first catalyst disclosed herein used in the subsequent dehydration reaction (production of acrolein and by products from first product comprising ethylene glycol, propylene glycol, and glycerol) deactivate rapidly in presence of ethylene glycol. FIG. 2 shows conversion of propylene glycol on 20-WO$_3$/SiO$_2$ (APT) catalyst with reaction time and corresponding selectivity to ethylene glycol formation. The conversion drops with formation of ethylene glycol due to catalyst deactivation. Accordingly, the method disclosed herein separates ethylene glycol and propylene glycol from the first product prior to conversion of the glycerol to acrolein and hydroxyacetone.

Figure 6:
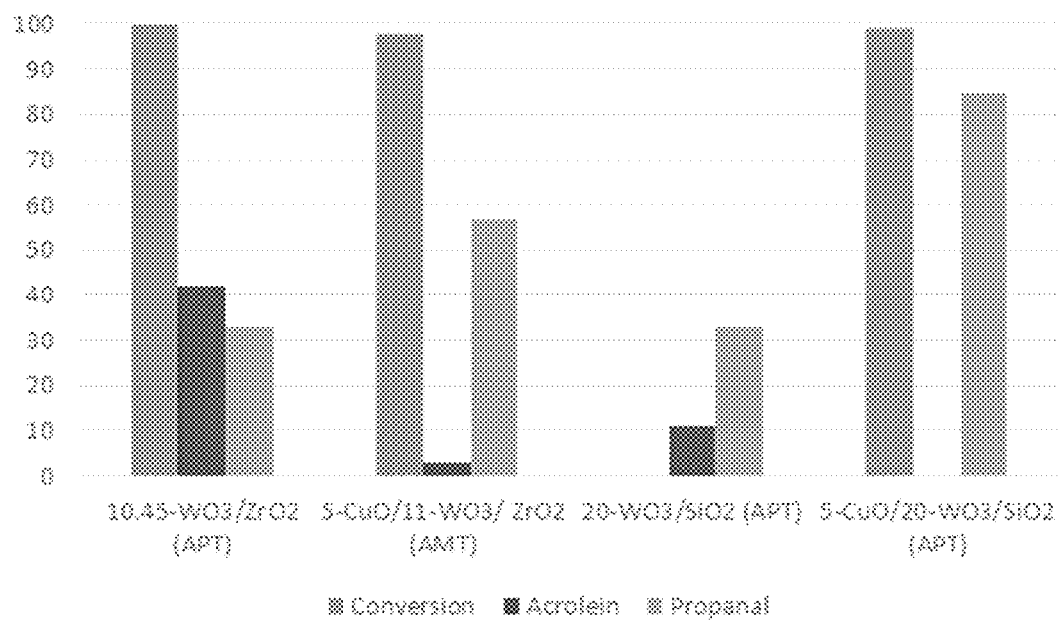
FIG. 6 shows the catalytic performance for propylene glycol conversion.

Furthermore, glycerol can be converted to acrolein at a high conversion and selectivity using the first catalyst disclosed herein. The catalytic performance was correlated with higher ratio of Bronsted to Lewis acidity of the catalysts used. However, same catalysts were shown to be less selective for propylene glycol conversion to acrolein, as shown in FIG. 6.

4. Aspen Simulations

Figure 12:
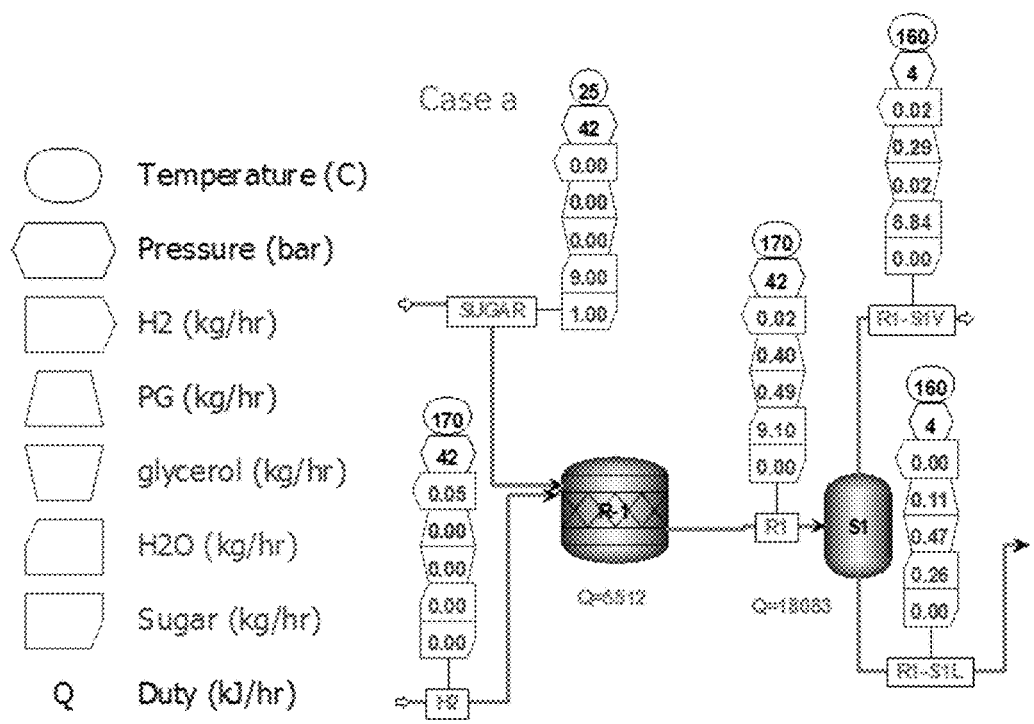
FIG. 12 shows ASPEN simulations of a method disclosed herein.
Figure 12:
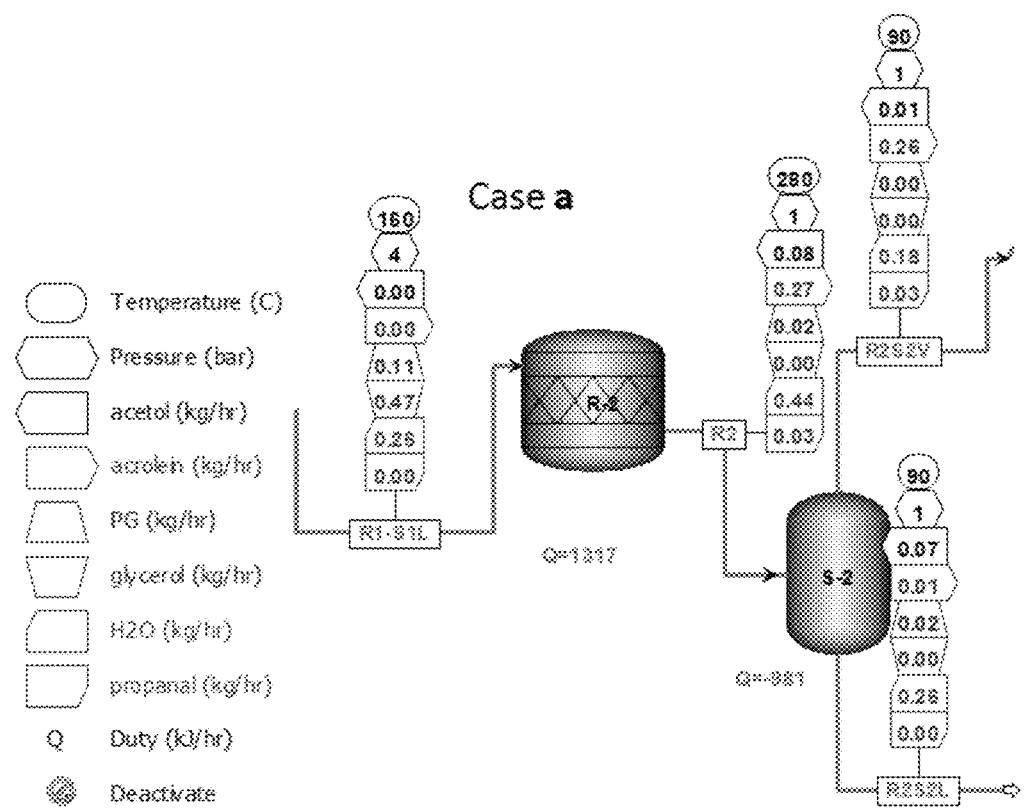
Figure 12:
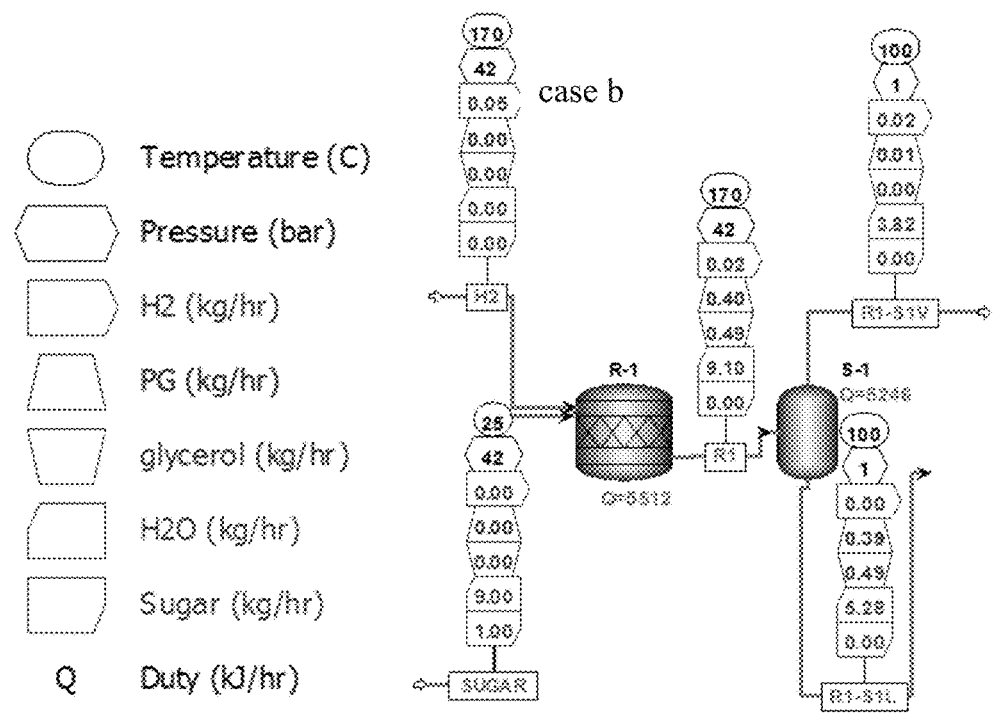
Figure 12:
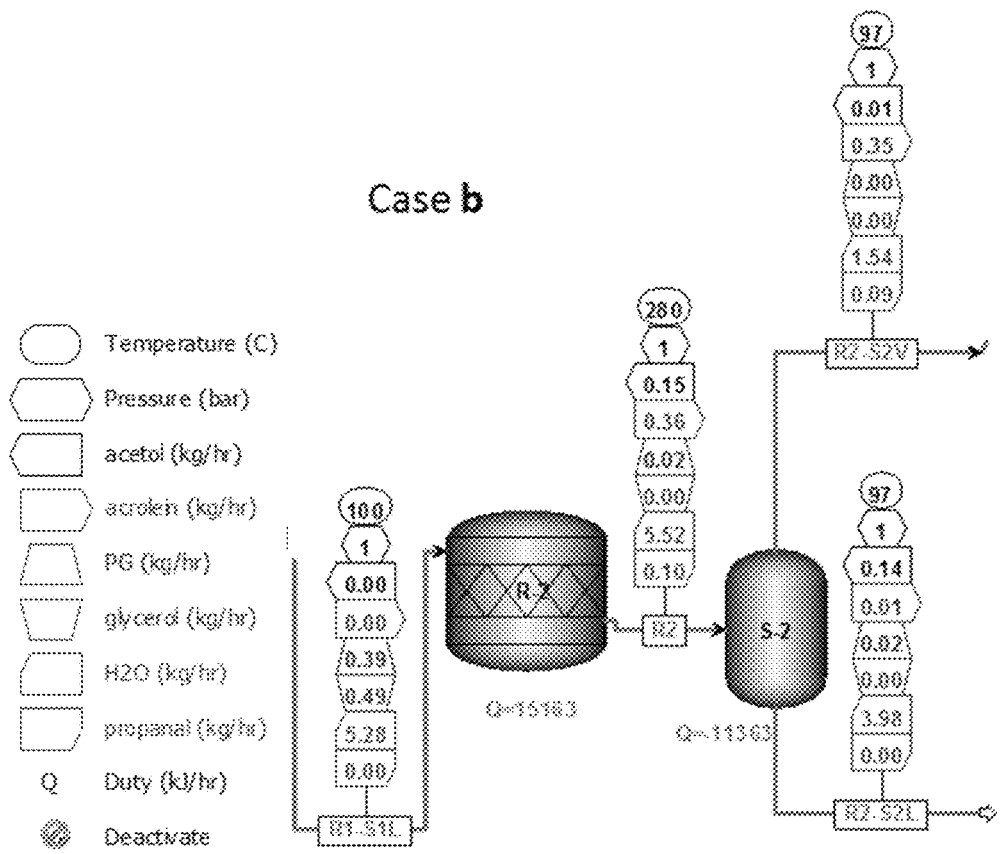

Aspen simulations were performed to compare: 1) a method where propylene glycol and ethylene glycol are separated from the first product prior to conversion of glycerol to acrolein and hydroxyacetone (case a); and 2) a method where propylene glycol and ethylene glycol are not separated from the first product prior to conversion of the first product to acrolein and by products (case b), see FIG. 12.

The detail specifications of the products produced in FIG. 12 are shown in Table 6 below.

TABLE 6

| Property | Case a | Case b |
|---|---|---|
| Desired product | Glycerol | Glycerol, PG |
| Selectivity (mol %) | Glycerol: PG = 1:1, EG <5% | Glycerol:PG = 1:1, EG <5% |
| Separation unit & spec | Flash (1): 160° C., 4 bar | Flash (1): 100° C., 1 bar |
| Separation (R1S1-V) loss | $H_2O$ (97%), Glycerol (3%), PG (73%, to propanal) | $H_2O$ (43%), PG (2%) |
| Recovered stream (R1S1-L) composition (dry basis) | 79% Glycerol 19% PG | 53% Glycerol 40% PG |
| Desired product | Acrolein | Acrolein |
| Selectivity | 82% Glycerol → Acrolein 18% Glycerol → Acetol 40% PG → Acrolein 33% PG → Propanal 10% PG → Acetol | 82% Glycerol → Acrolein 18% Glycerol → Acetol 40% PG → Acrolein 33% PG → Propanal 10% PG → Acetol |
| Separation unit & spec | Flash (1): 90° C., 1 bar | Flash (1): 97° C., 1 bar |
| Separation (R2S2L) loss | $H_2O$ (59%), Acrolein (3.7%), Acetol (87%) | Water (72%), Acrolein (3%), Acetol (93%) |
| Recovered stream (R2S2V) composition (dry basis) | 87% Acrolein 3% Acetol 8% propanal | 74% acrolein 2% Acetol 22% propanal |

Post-reaction separation was set to be conducted using flash evaporation. The specification of the flash column has been set to ensure maximum propylene glycol, ethylene glycol and $H_2O$ separation (case a) or maximum $H_2O$ separation (case b) from the top stream (R1-S1V). In case a this top stream will be used to produce propanal from propylene glycol using the second or third catalyst composition disclosed herein.

In case a, however, both the produced PG and glycerol remain unseparated and are passed on to the next reaction step for acrolein conversion. Here significant difference arises in flash separation between case a and b. In case a, energy requirement is significantly higher due to heating all the water emerging out of Reactor 1 (R-1) at a higher temperature (conservative approach) and potentially in two separate steps and flash drums.

FIG. 12 also shows ASPEN diagrams of units around Reactor 2 (R-2). Here the difference between case a and b becomes obvious in the product stream (R2). For case a, acrolein is produced only from glycerol (0.27 lb acrolein/lb of sugar) whereas in case b it is produced both from propylene glycol and glycerol (0.36 lb/lb glycerol). However, considerable formation of propanal is noticeable in case b compared to case a (0.10 lb vs. 0.03 lb/lb sugar). As described herein, the separation of propanal from acrolein can be difficult due to similar boiling points and would require a multistage distillation column.

TABLE 7

| Desired product | Acrylonitrile | Acrylonitrile |
|---|---|---|
| Selectivity | 90% Acrolein → ACN 75% Propanal → $CO_2$ 25% Propanal → Propionitrile 10% Acrolein → $CO_2$ | 90% Acrolein → ACN 75% Propanal → $CO_2$ 25% Propanal → Propionitrile 10% Acrolein → $CO_2$ |
| Separation unit & spec | HE (1), Stripper (1), Distillation (1), Settling drum (1) | HE (1), Stripper (1), Distillation (1), Settling drum (1) |
| Separation loss | ACN (9%) | ACN (11%) |
| Recovered stream (ACN-F) composition (dry basis) | 98% ACN | 98% ACN |

Figure 13:
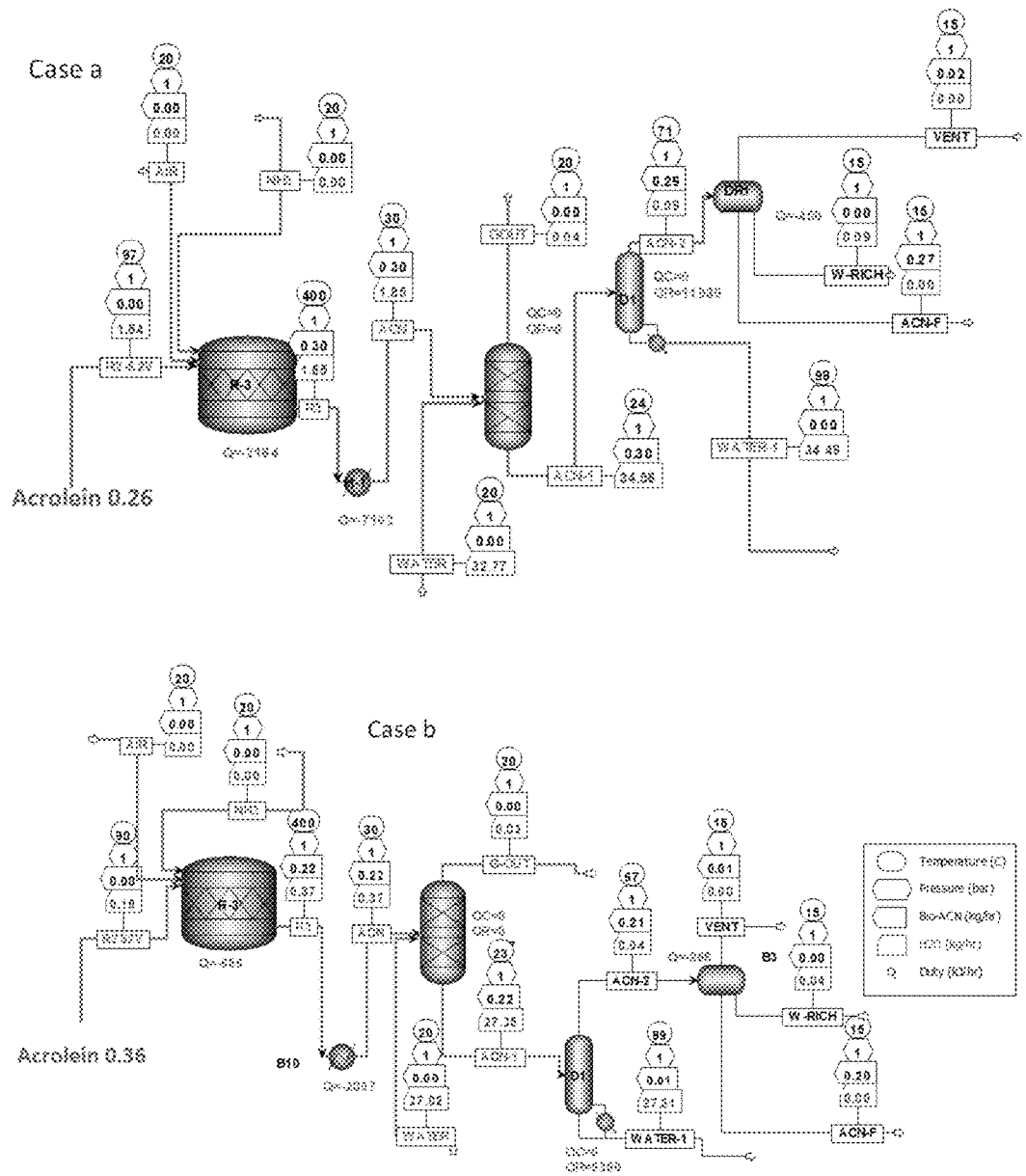
FIG. 13 shows ASPEN simulations of a method disclosed herein.

ASPEN calculations of the Ammoxidation step of acrolein in case a and case b is shown in FIG. 13. This reaction step is currently being studied. The performance of the catalyst is estimated from literature, and the separation and purification of ACN is also obtained from commercial process (Langvardt, P. W. 2011. Acrylonitrile. Ullmann's Encyclopedia of Industrial Chemistry). After purification the production of acrylonitrile is 0.20 lb/lb sugar for case a and 0.27 lb/lb sugar for case b). Table 7 above summarizes the ASPEN simulations for this process.

Various modifications and variations can be made to the compounds, composites, kits, articles, devices, compositions, and methods described herein. Other aspects of the compounds, composites, kits, articles, devices, compositions, and methods described herein will be apparent from consideration of the specification and practice of the compounds, composites, kits, articles, devices, compositions, and methods disclosed herein. It is intended that the specification and examples be considered as exemplary.

What is claimed is:
1. A method comprising the step of:
a) separating at least a portion of ethylene glycol and propylene glycol from a first product comprising ethylene glycol, propylene glycol, and glycerol, thereby producing a second product comprising glycerol; and
b) contacting the second product comprising glycerol with a first catalyst composition, thereby producing a third product comprising acrolein and hydroxyacetone,
wherein the first catalyst composition comprises a first catalyst comprising the formula:

wherein M2 is a metal with acid sites promoting dehydration,
wherein M3 is an amphoteric catalyst support, with acid and base sites,
wherein x is a molar ratio from about 0.25 to about 4,
wherein y is a molar ratio from about 0.25 to about 4, wherein z is the total amount of oxygen bound to M2, and M3, and corresponds to the sum of the oxidation states of M2, and M3.

2. The method of claim 1, wherein the method further comprises the steps of:
   c) separating at least a portion of the hydroxyacetone from the third product, thereby forming a fourth product comprising acrolein; and
   d) following step c) converting at least a portion of the acrolein in the fourth product to acrylonitrile.

3. The method of claim 1, wherein the method further comprises prior to step a), in a single step, converting C5 and/or C6 sugars to the first product comprising ethylene glycol, propylene glycol, and glycerol in the presence of a multifunctional catalyst.

4. The method of claim 1, wherein the method further comprises contacting at least a portion of the separated propylene glycol with a second catalyst composition, thereby producing propanal, wherein the second catalyst composition comprises a second catalyst having the formula:

$$M4M5_aM6_bO_z$$

wherein M4 is a metal with acid sites promoting dehydration,
wherein M5 is an amphoteric catalyst support, with acid and base sites, promoting selective dehydration in conjunction with M6 when present,
wherein M6 is a metal promoting C—O cleavage,
wherein a is a molar ratio from about 0.25 to about 4,
wherein b is a molar ratio from 0 to about 4,
wherein z is the total amount of oxygen bound to M4, M5, and M6, and corresponds to the sum of the oxidation states of M4, M5, and M6.

5. The method of claim 1, wherein M2 is selected from the group consisting of W, Fe, P, and, a zeolite.

6. The method of claim 1, wherein M3 is selected from the group consisting of Zr, Al, Si, Mg, Ti, La, and Ce.

7. The method of claim 1, wherein M2 is W.

8. The method of claim 1, wherein M3 is Zr.

9. The method of claim 1, wherein the first catalyst has the formula $WO_3ZrO_2$ or $WO_3SiO_2$.

10. The method of claim 3, wherein the C5 and/or C6 sugars is C5 and/or C6 hemicellulose and cellulose derived sugars.

11. The method of claim 3, wherein the multifunctional catalyst comprises one or more metals selected from the group consisting of Cu, Zn, Sn, Ni, Pt, Pd, Ru, and Re, and a support.

12. The method of claim 11, wherein the support is selected from the group consisting of $Al_2O_3$, $SiO_2$, carbon, $TiO_2$, and MgO.

13. The method of claim 1, wherein at least 60 wt % of the propylene glycol is separated from the first product.

14. The method of claim 1, wherein the third product comprises at least 50 wt % of acrolein.

15. The method of claim 1, wherein the second product comprises at least 2 times more glycerol than propylene glycol by weight.

16. The method of claim 1, wherein the first catalyst further comprises M1, wherein M1 is a metal promoting C—O cleavage,
   wherein M2 and M3 promotes selective dehydration in conjunction with M1,
   wherein z is the total amount of oxygen bound to M1, M2, and M3, and corresponds to the sum of the oxidation states of M1, M2, and M3.

17. The method of claim 16, wherein M1 is selected from the group consisting of Cu, Zn, and Sn.

18. The method of claim 16, wherein M1 is Cu.

19. The method of claim 4, wherein
   M4 is selected from the group consisting of W, Fe, P, and a zeolite,
   M5 is selected from the group consisting of Zr, Al, Si, Mg, Ti, La, and Ce, and
   M6 is selected from the group consisting of Cu, Zn, and Sn.

20. The method of claim 19, wherein the first catalyst has the formula $WO_3ZrO_2$ or $WO_3SiO_2$.

* * * * *